(12) United States Patent
Hossain et al.

(10) Patent No.: US 11,819,825 B1
(45) Date of Patent: Nov. 21, 2023

(54) VANADIUM-BASED CATALYST COMPOSITION FOR $CO_2$-MEDIATED OXIDATIVE DEHYDROGENATION OF PROPANE

(71) Applicant: KING FAHD UNIVERSITY OF PETROLEUM AND MINERALS, Dhahran (SA)

(72) Inventors: Mohammad M. Hossain, Dhahran (SA); Yahya Gambo, Dhahran (SA); Mohammed S. Ba-Shammakh, Dhahran (SA); Akolade Idris Bakare, Dhahran (SA); Sagir Adamu, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/300,976

(22) Filed: Apr. 14, 2023

(51) Int. Cl.
*B01J 23/22* (2006.01)
*B01J 23/02* (2006.01)
(Continued)

(52) U.S. Cl.
CPC .............. *B01J 23/22* (2013.01); *B01J 21/16* (2013.01); *B01J 23/02* (2013.01); *B01J 35/006* (2013.01);
(Continued)

(58) Field of Classification Search
CPC ... B01J 23/22; B01J 21/16; B01J 23/02; B01J 35/0013; B01J 35/006; B01J 35/026;
(Continued)

(56) References Cited

U.S. PATENT DOCUMENTS 4,169,927 A * 10/1979 Hill .................. C08F 10/02
502/120
4,284,530 A * 8/1981 Sherif .................. C01B 17/79
423/535
(Continued)

FOREIGN PATENT DOCUMENTS

| CN | 112642418 A | 4/2021 |
| CN | 113893851 A | 1/2022 |
| CN | 112723971 B | 10/2022 |

OTHER PUBLICATIONS

Otroschchenko et al. ; Current status and perspectives in oxidative, non-oxidative and CO2-mediated dehydrogenation of propane and isobutane over metal oxide catalysts ; Royal Society of Chemistry ; Nov. 18, 2020 ; 2 Pages ; Abstract Only.

(Continued)

*Primary Examiner* — Ali Z Fadhel
(74) *Attorney, Agent, or Firm* — Oblon, McClelland, Maier & Neustadt, L.L.P.

(57) ABSTRACT

A method of making an active catalyst composition includes mixing at least one support with a vanadium oxide precursor and grinding thereby at least partially embedding the vanadium oxide precursor particles in different layers and surfaces of the at least one support to form a first precursor; mixing the first precursor and a first solvent to form a first mixture; grinding the first mixture and drying at a temperature of 60 to 105° C.; calcining the first mixture after the drying at a temperature of at least 300° C. thereby allowing the vanadium oxide precursor particles embedded in different layers and surfaces of the at least one support to decompose in situ to generate vanadium oxide ($VO_x$) particles embedded in the at least one support and form the first vanadium catalyst; and mixing the first vanadium catalyst with a second vanadium catalyst to form the active catalyst composition.

20 Claims, 18 Drawing Sheets

(51) Int. Cl.
*B01J 35/00* (2006.01)
*B01J 35/02* (2006.01)
*B01J 35/10* (2006.01)
*B01J 37/04* (2006.01)
*B01J 37/00* (2006.01)
*B01J 37/08* (2006.01)
*C07C 5/48* (2006.01)
*B01J 21/16* (2006.01)
*C11D 3/12* (2006.01)

(52) U.S. Cl.
CPC ......... *B01J 35/0013* (2013.01); *B01J 35/026* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 37/0036* (2013.01); *B01J 37/0045* (2013.01); *B01J 37/04* (2013.01); *B01J 37/086* (2013.01); *C07C 5/48* (2013.01); *C11D 3/1253* (2013.01); *C07C 2521/10* (2013.01); *C07C 2523/22* (2013.01)

(58) Field of Classification Search
CPC ............... B01J 35/1014; B01J 35/1019; B01J 35/1038; B01J 35/1042; B01J 35/1061; B01J 37/0036; B01J 37/0045; B01J 37/04; B01J 37/086; C07C 5/48; C07C 2521/10; C07C 2523/22; C11D 3/1253
See application file for complete search history.

(56) References Cited

U.S. PATENT DOCUMENTS 4,722,918 A * 2/1988 Schneider ................ B01J 23/28
502/81
2018/0346394 A1 12/2018 Almusaiteer et al.
2022/0111359 A1 4/2022 Miller et al.

OTHER PUBLICATIONS

Miranda et al. ; Oxidative dehydrogenation of propane: Developing catalysts containing VOx, V—P—O and V—Mg—O species supported on MCM-41 and activated carbon ; Catalysts Today, vol. 348 ; May 15, 2020 ; 4 Pages.

* cited by examiner

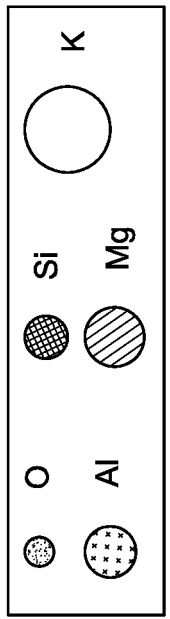
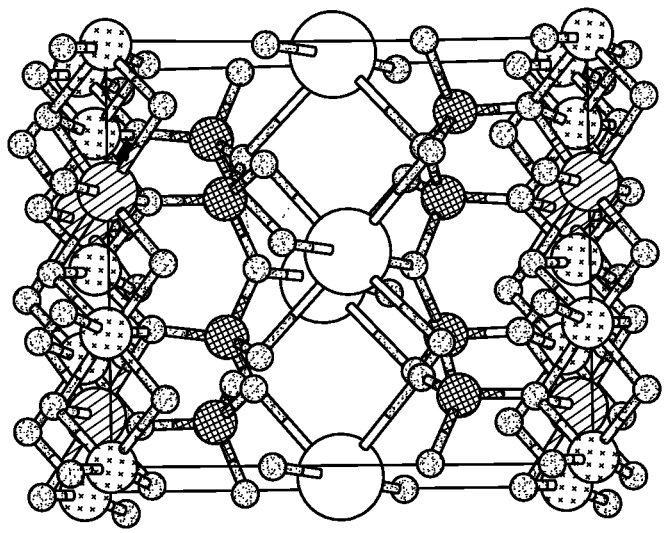
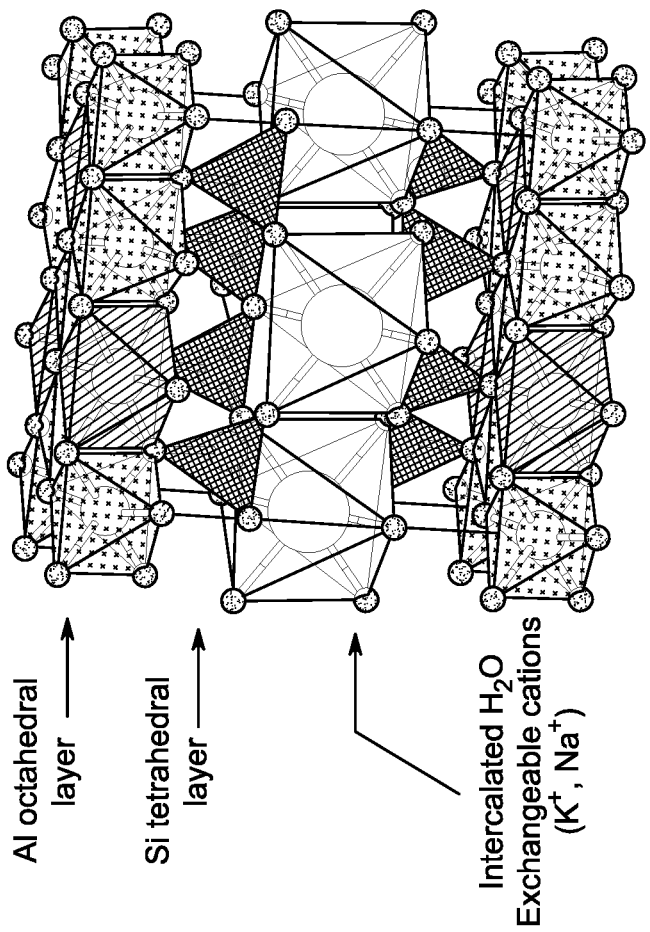
FIG. 1A
FIG. 1B

Model 1:
VOx/Mont + MgO

Model 2:
Mont + VOx/MgO

Model 3:
VOx/(Mont + MgO)

VANADIUM-BASED CATALYST COMPOSITION FOR CO$_2$-MEDIATED OXIDATIVE DEHYDROGENATION OF PROPANE

BACKGROUND

Technical Field

The present disclosure is directed to a catalyst, particularly a vanadium-based catalyst composition for CO$_2$-mediated oxidative dehydrogenation of propane, and a method of making the catalyst.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Advances in heterogeneous catalysis have enabled a vital platform to facilitate upgrading underutilized alkane feedstock, especially towards realizing sustainable alternatives to meet increased global demand for olefins. Light olefins such as propylene and ethylene are main platform chemicals with diverse applications in the petrochemical industry. Thus, the quest to develop on-purpose technologies for the production of these materials from underutilized alkane feedstock has remained a grand challenge in the contemporary field of catalysis.

Catalytic propane dehydrogenation (PDH) as a selective process has received booming investment with many ongoing installation plants globally. However, the highly energy-intensive process is strongly thermodynamically constrained by low per-pass conversions and suffers rapid catalyst deactivation due to coke formation. To offset the thermodynamic limitation and external heat requirement of the PDH, the process could be facilitated via oxidative mode using molecular oxygen. Still, poor selectivity control due to overoxidation of the hydrocarbon feedstock and generated olefins remains a significant problem. Alternatively, utilizing $CO_2$ as a soft oxidant provides a promising option to overcome the challenge and enable an alternative for $CO_2$ utilization. The process is called $CO_2$-mediated oxidative dehydrogenation ($CO_2$-ODH).

Vanadium- and chromium-based catalysts are among the most studied catalysts for the $CO_2$-ODH process and other selective redox processes, largely due to their tuneable surface properties and promising performances. In addition, relatively low cost and mild toxicity of vanadium make it uniquely suitable for various applications. Tuning and design strategies for the $VO_x$-based catalysts include stabilizing $VO_x$-based catalysts on suitable supports such as mesoporous silica, promoted MCM-41, modified $\gamma$-$Al_2O_3$, sulfated-zirconia, H-ZSM-5, and mixed metal oxides such as Ce—Zr and hybrid $TiO_2$—$ZrO_2$.

From another perspective, clays have found several applications as support materials in developing heterogeneous catalysts. Bahranowski et al. [K. Bahranowski, R. Grabowski, B. Grzybowska, A. Kielski, E. M. Serwicka, K. Wcislo, E. Wisla-Walsh, K. Wodnicka, Top. Catal. 11-12 (2000) 255-261] describes the use of clay supports in oxidative dehydrogenation (ODH) of light alkanes. Incorporating small metal and metal oxide clusters into the interlamellar spaces of layered clays such as montmorillonite can enable the development of suitable porous catalysts with remarkable active site accessibility. The process can be engineered via a facile one-step synthetic route. Cr—Al pillared montmorillonite clay exhibited promising low-temperature ODH performance, with a propylene yield of around 10.3% at 450° C.

Although a few catalyst compositions have been developed on montmorillonite in the past, these catalytic compositions have drawbacks such as low yield, high CO selectivity, and non-environmentally friendly synthetic methods. Accordingly, one objective of the present disclosure is to provide a catalytic composition by incorporating clay materials such as montmorillonite on vanadium utilizing green and sustainable precursors coupled with environmentally friendly protocols for the development of efficient $CO_2$-ODH catalysts. A further objective of the present disclosure is to describe a method for producing propylene via oxidative dehydrogenation of propane.

SUMMARY

In an exemplary embodiment, a method of making an active catalyst composition containing a first vanadium catalyst and a second vanadium catalyst is described. The method includes mixing at least one support with a vanadium oxide precursor and grinding thereby at least partially embedding the vanadium oxide precursor particles in different layers and surfaces of the at least one support to form a first precursor. The method includes mixing the first precursor and a first solvent to form a first mixture. The method further includes grinding the first mixture and drying at a temperature of 60 to 105° C. Additionally, the method involves calcining the first mixture after the drying at a temperature of at least 300° C. thereby allowing the vanadium oxide precursor particles embedded in different layers and surfaces of the at least one support to decompose in situ to generate vanadium oxide ($VO_x$) particles embedded in the at least one support and form the first vanadium catalyst. The method further involves mixing the first vanadium catalyst with the second vanadium catalyst to form the active catalyst composition. In some embodiments, a weight ratio of the at least one support to the vanadium oxide precursor is in a range of 100:1 to 10:1. In some embodiments, the vanadium oxide particles have an average particle size of 50 to 200 nanometers (nm), and are uniformly distributed throughout the first vanadium catalyst, in which 0<x<3. In some embodiments, the at least one support comprises a smectite clay and a metal oxide.

In some embodiments, the vanadium oxide precursor is at least one selected from the group consisting of vanadium acetylacetonate, ammonium vanadate, vanadyl oxalate, vanadium pentoxide, vanadium monoethanolamine, vanadium chloride, vanadium trichloride oxide, vanadyl sulfate, vanadium antimonate, antimony vanadate, vanadium oxyacetylacetonate, vanadium oxyacetate, vanadium oxyhalide, and vanadium oxytriisopropoxide.

In some embodiments, the vanadium oxide ($VO_x$) particles comprise vanadium monoxide (VO), vanadium trioxide ($V_2O_3$), vanadium dioxide ($VO_2$), and vanadium pentoxide ($V_2O_5$).

In some embodiments, the first solvent is at least one selected from the group consisting of a ketone solvent, an ester solvent, an alcohol solvent, an amide solvent, and an ether solvent.

In some embodiments, the first precursor is present in the first mixture at a concentration of 1 to 40 wt. % based on a total weight of the first mixture.

In some embodiments, the smectite clay comprises at least one clay selected from the group consisting of montmorillonite (Mont), nontronite, beidellite, bentonite, bolcon score, laponite, hectorite, saponite, soconite, magadiite, kenyaite, stevensite, vermiculite, halloysite, and hydrotalcite.

In some embodiments, the smectite clay is montmorillonite, wherein the montmorillonite has a delaminated-pillared structure. In some embodiments, the delaminated-pillared structure comprising an aluminosilicate framework having a tetrahedral silicate layer and an octahedral aluminium hydroxide layer. In some embodiments, a plurality of exchangeable intercalated cations between two adjacent aluminosilicate frameworks.

In some embodiments, the metal oxide comprises at least one selected from the group consisting of magnesium oxide (MgO), aluminum oxide ($Al_2O_3$), and titanium oxide ($TiO_2$).

In some embodiments, the method further includes forming the second vanadium catalyst by mixing the first vanadium catalyst with a second support and grinding to form a second precursor. The method further includes mixing the second precursor and a second solvent to form a second mixture; grinding the second mixture and drying at a temperature of 60 to 105° C.; and calcining the second mixture after the drying at a temperature of at least 300° C. to form the second vanadium catalyst. In some embodiments, a weight ratio of the first vanadium catalyst to the second support is in a range of 2:1 to 1:2. In some embodiments, the first vanadium catalyst is complexed with the second support. In some embodiments, the second support comprises a smectite clay and a metal oxide.

In some embodiments, the smectite clay is montmorillonite (Mont), and the metal oxide is MgO. In some embodiments, the active catalyst composition is at least one selected from the group consisting of a MgO supported vanadium (MgV), a Mont supported vanadium (MontV), a Mont supported vanadium supported on MgO((MontV)Mg), a MgO supported vanadium supported on Mont (Mont (MgV)), and a Mont/MgO co-supported vanadium ((MontMg)V).

In some embodiments, the active catalyst composition has a multi-layered mesoporous structure.

In some embodiments, the active catalyst composition has a specific surface area in a range of 50 to 200 square meters per gram ($m^2/g$).

In some embodiments, the active catalyst composition has a cumulative specific pore volume in a range of 0.1 to 0.8 cubic centimeters per gram ($cm^3/g$).

In some embodiments, the active catalyst composition has an average pore diameter of 50 to 300 angstroms (Å).

In an exemplary embodiment, a method for producing propylene via oxidative dehydrogenation (ODH) of propane is described. The method includes introducing a feed gas stream containing $CO_2$ and propane into a reactor containing the active catalyst composition; passing the feed gas stream through the reactor in the presence of the active catalyst composition at a temperature of 300 to 900° C. to convert at least a portion of the propane to propylene and produce a propylene-containing gas stream leaving the reactor; and separating the propylene from the propylene-containing gas stream.

In some embodiments, a volume ratio of $CO_2$ to propane in the feed gas stream is in a range of 1:10 to 10:1.

In some embodiments, the propylene-containing gas stream further comprises methane, ethane, ethylene, propane, carbon monoxide, carbon dioxide, hydrocarbon containing $C_4$-$C_5$, and aromatics.

In some embodiments, the method has a propane conversion to propylene of up to 80 wt. % based on an initial weight of the propane in the feed gas stream.

In some embodiments, the method has a propylene yield of up to 40% based on the propane conversion according to equation $Y_3 = (X_{C_3H_8} * S_3) \times 100\%$. In some embodiments, $X_{C_3H_8}$ denotes the propane conversion to propylene, and $S_3$ denotes the propylene selectivity.

In some embodiments, the method has a propylene selectivity of up to 70.% based on the propane conversion according to equation $$S_3 = \frac{n_3}{n_{C_3H_{8_{in}}} - n_{C_3H_{8_{out}}}} \times 100\%.$$

In some embodiments, $S_3$ denotes the propylene selectivity, $(n_{C_3H_8})_{in}$ and $((n_{C_3H_8})_{out}$ denote the inlet and outlet moles of the propane in the feed gas stream containing $CO_2$ and propane, respectively, and $n_3$ denote moles of the propylene in the propylene-containing gas stream leaving the reactor.

The foregoing general description of the illustrative present disclosure and the following The detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 1A depicts a structure of a typical montmorillonite unit cell as a polyhedral model drawn using VESTA®;

FIG. 1B depicts a structure of the typical montmorillonite unit cell as a ball-and-stick model drawn using VESTA®;

DETAILED DESCRIPTION

Figure 2A:
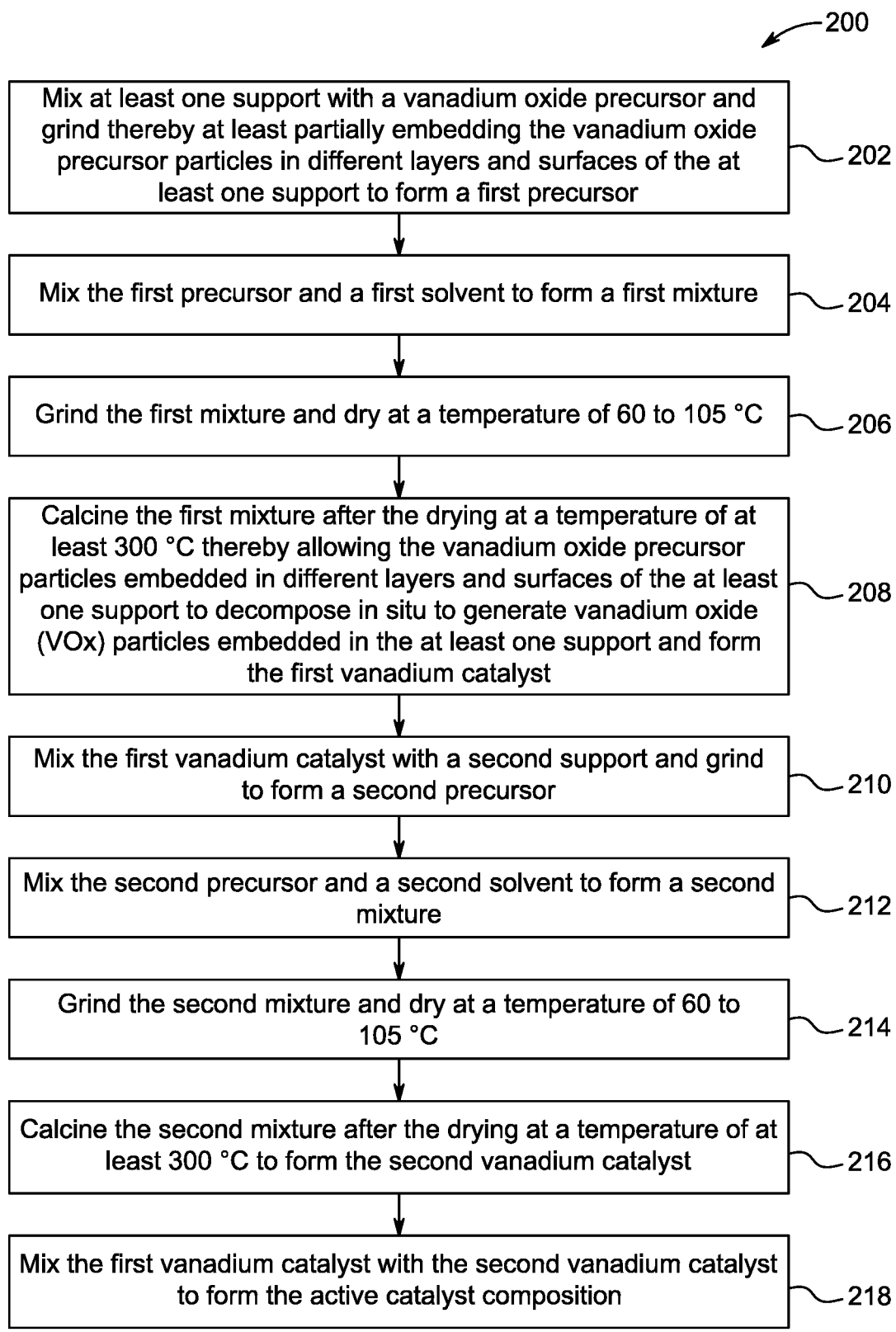
FIG. 2A is a flow chart depicting a method of making an active catalyst composition, according to certain embodiments.

In the drawings, reference numerals designate identical or corresponding parts throughout the several views. Further, as used herein, the words "a," "an," and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term 'calcination' refers to the thermal treatment of a solid chemical compound whereby the compound is raised to a high temperature without melting under a restricted supply of ambient oxygen, generally for the purpose of removing impurities or volatile substances and to incur thermal decomposition.

Aspects of the present disclosure are directed to the development of $VO_x$-based catalysts, deliberately configured to harness possible synergy among montmorillonite (Mont) and MgO as support materials. The facile synthesis strategy exploits the spatial integration of the individual supports via physical grinding, e.g., in a mortar, to yield the integrated catalysts.

Referring to FIG. 2A, a schematic flow diagram of the method 200 of making an active catalyst composition containing a first vanadium catalyst and a second vanadium catalyst is illustrated. The order in which the method 200 is described is not intended to be construed as a limitation, and any number of the described method steps may be combined in any order to implement the method 200. Additionally, individual steps may be removed or skipped from the method 200 without departing from the spirit and scope of the present disclosure.

At step 202, the method 200 includes mixing at least one support with a vanadium oxide precursor and grinding thereby at least partially embedding the vanadium oxide precursor particles in different layers and surfaces of the at least one support to form a first precursor. In some embodiments, the support includes one or both of a smectite clay and a metal oxide. Smectite clay may be procured commercially or may be synthesized by processes known in the art (synthetic smectite). The synthetic smectite closely resembles the natural clay mineral hectorite in both structure and composition. Hectorite is a natural swelling clay that is relatively rare and occurs contaminated with other minerals such as quartz which are difficult and expensive to remove. Synthetic smectite is free from natural impurities and prepared under controlled conditions. The synthetic smectite is a layered hydrous magnesium silicate, in which magnesium ions, partially replaced by suitable monovalent ions such as lithium, sodium, potassium, and/or vacancies, are octahedrally coordinated to oxygen and/or hydroxyl ions, some of which may be replaced by fluorine ions, forming the central octahedral sheet. Such an octahedral sheet is sandwiched between two tetrahedral sheets of silicon ions, tetrahedrally coordinated to oxygen.

In some embodiments, the smectite clay includes at least one clay selected from montmorillonite (Mont), nontronite, beidellite, bentonite, bolcon score, laponite, hectorite, saponite, soconite, magadiite, kenyaite, stevensite, vermiculite, halloysite, and hydrotalcite. In a preferred embodiment, the smectite clay is montmorillonite. The montmorillonite has a delaminated-pillared structure including an aluminosilicate framework having a tetrahedral silicate layer and an octahedral aluminum hydroxide layer. The delaminated-pillared structure further includes a plurality of exchangeable intercalated cations between two adjacent aluminosilicate frameworks. FIG. 1A and FIG. 1B depicts the typical structural model of a montmorillonite unit cell, as a polyhedral model and a ball-and-stick model, respectively, with a well-defined negatively charged aluminosilicate layer composed of ordered tetrahedral $[SiO_4]^{4-}$ and octahedral $[AlO_3(OH)_3]^{6-}$ layers. The pillared interlayered clays (PILCs) usually exhibit a shorter diffusion path, which could be exploited to significantly limit the chances of olefins overoxidation in ODH reactions.

In some embodiments, the metal oxide comprises at least one selected from magnesium oxide (MgO), aluminum oxide ($Al_2O_3$), and titanium oxide ($TiO_2$). In a preferred embodiment, the smectite clay is Mont, and the metal oxide is MgO. Optionally, other support materials, such as silica, silica gel, alumina, titania, silica/alumina, calcium metasilicate, pyrogenic silica, high purity silica, zirconia, carbon, zeolites, and mixtures thereof, can be incorporated as well (albeit with a few variations, as may be obvious to a person skilled in the art). In some embodiments, the support may be impregnated with promoters. Suitable examples of the promoters include one or more transition metals, one or more transition metal-containing compounds, alkali metals, alkali-metal-containing compounds, or combinations thereof.

The support (including the smectite clay and/or the metal oxide) is mixed with the vanadium oxide precursor and ground together to form the composite. The vanadium oxide precursor is at least one selected from the group consisting of vanadium acetylacetonate, ammonium vanadate, vanadyl oxalate, vanadium pentoxide, vanadium monoethanolamine, vanadium chloride, vanadium trichloride oxide, vanadyl sulfate, vanadium antimonate, antimony vanadate, vanadium oxyacetylacetonate, vanadium oxyacetate, vanadium oxyhalide, and vanadium oxytriisopropoxide. In a preferred embodiment, the vanadium oxide precursor is vanadium (III) acetylacetonate. In some embodiments, the weight ratio of the support to the vanadium oxide precursor is in a range of 100:1 to 10:1, preferably 90:1 to 20:1, preferably 80:1 to 30:1, preferably 70:1 to 40:1, or even more preferably 60:1 to 50:1. The vanadium oxide precursor is mixed with the support and ground for 1-120 minutes, preferably 5-60 minutes, or even more preferably 5-10 minutes, to obtain the composite. Other ranges are also possible.

In some embodiments, vanadium oxide precursor particles are at least partially embedded in different layers and surfaces of the at least one support. In some embodiments, at least 30% by number of the vanadium oxide precursor particles are embedded in different layers of the at least one support, preferably at least 50%, preferably at least 70%, or even more preferably at least 90%. In some further embodiments, no more than 95% by number of the vanadium oxide precursor particles are at embedded in different layers of the at least one support, preferably no more than 75%, preferably no more than 55%, or even more preferably no more than 35%. In some preferred embodiments, at least 10% by number of the vanadium oxide precursor particles are at embedded in surfaces of the at least one support, preferably at least 30%, preferably at least 50%, or even more preferably at least 70%. In some more preferred embodiments, no more than 75% by number of the vanadium oxide precursor particles are at embedded in surfaces of the at least one support, preferably no more than 55%, preferably no more than 35%, or even more preferably no more than 15%. Other ranges are also possible.

At step 204, the method 200 includes mixing the first precursor and a first solvent to form a first mixture. The first solvent is at least one selected from the group consisting of a ketone solvent, an ester solvent, an alcohol solvent, an amide solvent, and an ether solvent. In some embodiments, the first solvent is an alcohol—such as ethanol, isopropyl alcohol, etc. In a preferred embodiment, the first solvent is ethanol. In some embodiments, the first precursor is present in the first mixture at a concentration of 1 to 40 wt. % based on the total weight of the first mixture, preferably 5 to 35 wt. %, preferably 10 to 30 wt. %, preferably 15 to 25 wt. %, or even more preferably about 20 wt. % based on the total weight of the first mixture. Other ranges are also possible.

At step 206, the method 200 includes grinding the first mixture and drying at a temperature of 60 to 105° C., preferably 70 to 95° C., or even more preferably 80 to 85° C. In some embodiments, the first mixture was ground for 1 to 60 minutes, preferably 2-30 minutes, preferably 5-10 minutes, or even more preferably about 5 minutes, till the first mixture was dispersed entirely in the composite. The first mixture was further dried to a temperature of 70 to 100° C., preferably 80-100° C., preferably 95° C. to evaporate the solvent molecules from the first mixture. The drying process was carried out in an oven for 1-5 hours, preferably 2-4 hours, or more preferably for 2 hours. Other ranges are also possible.

At step 208, the method 200 includes calcining the first mixture after the drying at a temperature of at least 300° C. thereby allowing the vanadium oxide precursor particles embedded in different layers and surfaces of the at least one support to decompose in situ to generate vanadium oxide ($VO_x$) particles embedded in the at least one support and form the first vanadium catalyst. The calcination process may be performed in one or two steps. In some embodiments, the calcination was carried out by heating the first mixture to a temperature range of 200-400° C., preferably to about 300° C. at a heating rate of 1-20° C./min, preferably 3-15° C./min, preferably 5-10° C./min, more preferably at about 5° C./min. This process was carried out for about 1-5 hours, preferably 2-3 hours, and more preferably for about 3 hours. In some other embodiments, the calcination process involves two steps—for example, in the first step, the calcination was carried out by heating the first mixture to a temperature range of 200-400° C., preferably to about 300° C. at a heating rate of 1-20° C./min, preferably 3-15° C./min, preferably 5-10° C./min, more preferably at about 5° C./min. This process was carried out for about 1-5 hours, preferably 2-3 hours, and more preferably for about 3 hours. In the second step, the first mixture was further heated to a temperature range of 500° C.-800° C., preferably 550-750° C., preferably 600-650° C., and more preferably to about 600° C. at a heating rate of 1-20° C./min, preferably 3-15°

C./min, preferably 5-10° C./min, more preferably at about 5° C./min. This step was carried out for 1-10 hours, preferably 2-5 hours, and more preferably to about 3 hours. The calcination may be performed by any conventional method or apparatus known to a person skilled in the art, for example, but not limited to, using a muffle furnace, electric furnace, tube furnace, box furnace, crucible furnace, microwave furnace, vacuum furnace, rotary kiln, or fluidized bed furnace. The two-step calcination process decomposes the vanadium oxide precursor to form the vanadium oxide ($VO_x$) particles with an average particle size in a range of 50 to 200 nm, preferably 75 to 175 nm, preferably 50 to 150 nm, preferably 75 to 125 nm, or even more preferably about 100 nm. Other ranges are also possible.

In some embodiments, the vanadium oxide precursor particles embedded in different layers and surfaces of the at least one support decomposes in situ during the calcining to generate the vanadium oxide ($VO_x$). In some embodiments, at least 50% by number of the vanadium oxide precursor particles are decomposed to generate the vanadium oxide particles. In some embodiments, at least 30% by number of the vanadium oxide particles are at embedded in different layers of the at least one support, preferably at least 50%, preferably at least 70%, or even more preferably at least 90%. In some further embodiments, no more than 95% by number of the vanadium oxide particles are at embedded in different layers of the at least one support, preferably no more than 75%, preferably no more than 55%, or even more preferably no more than 35%. In some preferred embodiments, at least 10% by number of the vanadium oxide particles are at embedded in surfaces of the at least one support, preferably at least 30%, preferably at least 50%, or even more preferably at least 70%. In some more preferred embodiments, no more than 75% by number of the vanadium oxide particles are at embedded in surfaces of the at least one support, preferably no more than 55%, preferably no more than 35%, or even more preferably no more than 15%. Other ranges are also possible.

The vanadium oxide particles may be of any shape, such as spherical, cubical, ellipsoid, and the like. In a preferred embodiment, the vanadium oxide particles are spherical. In some embodiments, the vanadium oxide particles are uniformly distributed throughout the first vanadium catalyst. In some further embodiments, the vanadium in the $VO_x$ particles may exist in various oxidation states, such as +2, +3, +4, and +5. The $VO_x$ includes vanadium monoxide (VO), vanadium trioxide ($V_2O_3$), vanadium dioxide ($VO_2$), and vanadium pentoxide ($V_2O_5$). In a preferred embodiment, vanadium oxide ($VO_x$) particles include VO and $VO_2$ (0<x<3). The $VO_x$ particles have an average particle size of 50 to 200 nm and are uniformly distributed throughout the first vanadium catalyst composition, where 0<x<3.

At step 210, the method 200 includes mixing the first vanadium catalyst with a second support and grinding to form a second precursor. The second support includes one or both of smectite clay, and a metal oxide. The metal oxide comprises at least one selected from magnesium oxide (MgO), aluminum oxide ($Al_2O_3$), and titanium oxide ($TiO_2$). In a preferred embodiment, the metal oxide is MgO. The second support may optionally include other support materials, such as silica, silica gel, alumina, titania, silica/alumina, calcium metasilicate, pyrogenic silica, high purity silica, zirconia, carbon, zeolites, and mixtures thereof. In some embodiments, the second support may be impregnated with promoters. Suitable examples of the promoters include one or more transition metals, one or more transition metal-containing compounds, alkali metals, alkali-metal-containing compounds, or combinations thereof. The first vanadium catalyst composition is complexed with the second support during the grinding process to form the second composite. In some embodiments, the weight ratio of the first vanadium catalyst composition to the second support is in a range of 2:1 to 1:2, preferably 3:2 to 2:3, or even more preferably about 1:1. Other ranges are also possible.

At step 212, the method 200 includes mixing the second precursor and a second solvent to form a second mixture. The second solvent is at least one selected from the group consisting of a ketone solvent, an ester solvent, an alcohol solvent, an amide solvent, and an ether solvent. In some embodiments, the solvent is alcohol—such as ethanol, isopropyl alcohol, etc. In a preferred embodiment, the solvent is ethanol.

At step 214, the method 200 includes grinding the second mixture and drying at a temperature of 60 to 105° C., preferably 70 to 95° C., or even more preferably 80 to 85° C. The second mixture was ground for 1 to 60 minutes, preferably 2-30 minutes, preferably 5-10 minutes, or even more preferably about 5 minutes, till the second mixture was dispersed entirely in the second composite. The mixture was further dried to a temperature of 70 to 100° C., preferably 80-100° C., preferably 95° C. to evaporate the solvent molecules from the mixture. The drying process was carried out in an oven for 1-5 hours, preferably 2-4 hours, or more preferably for 2 hours. Other ranges are also possible.

At step 216, the method 200 includes calcining the second mixture after the drying at a temperature of at least 300° C. to form the second vanadium catalyst. The calcination process may be performed in one or two steps. In some embodiments, the calcination was carried out by heating the second mixture to a temperature range of 200-400° C., preferably 250-3500° C., or even more preferably to about 300° C. at a heating rate of 1-20° C./min, preferably 3-15° C./min, preferably 5-10° C./min, more preferably at about 5° C./min. This process was carried out for about 1-5 hours, preferably 2-3 hours, and even more preferably for about 3 hours, to form the second vanadium catalyst. Other ranges are also possible.

Figure 3A:
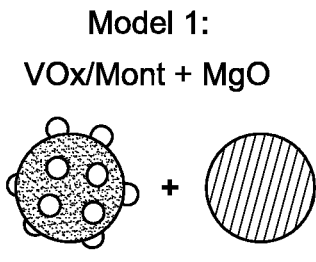
FIG. 3A is a schematic illustration depicting an integrated catalyst model, montmorillonite supported vanadium supported on MgO((MontV)Mg) or ($VO_x$/Mont+MgO), according to certain embodiments.
Figure 3B:
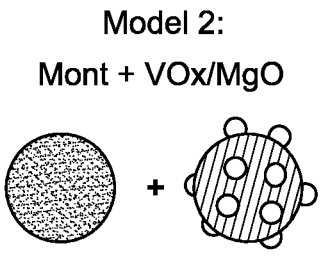
FIG. 3B is a schematic illustration depicting an integrated catalyst model, MgO supported vanadium supported on montmorillonite (Mont(MgV)) or (Mont+$VO_x$/MgO), according to certain embodiments.
Figure 3C:
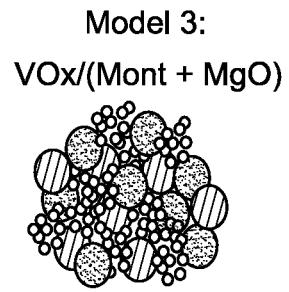
FIG. 3C is a schematic illustration depicting an integrated catalyst model, montmorillonite/MgO co-supported vanadium ((MontMg)V) or ($VO_x$/Mont+MgO), according to certain embodiments.

At step 218, the method 200 includes mixing the first vanadium catalyst with the second vanadium catalyst to form the active catalyst composition. The first vanadium catalyst and a second vanadium catalyst together form the active catalyst composition. Suitable examples of the active catalyst composition include MgO-supported vanadium (MgV), a Mont-supported vanadium (MontV), a Mont-supported vanadium supported on MgO((MontV)Mg) (FIG. 3A), a MgO-supported vanadium supported on Mont (Mont (MgV)) (FIG. 3B), and a Mont/MgO co-supported vanadium ((MontMg)V) (FIG. 3C). In some embodiments, the active catalyst composition has a multi-layered mesoporous structure with a cumulative specific pore volume in a range of 0.1 to 0.8 $cm^3/g$, preferably 0.2 to 0.7 $cm^3/g$, preferably 0.3 to 0.6 $cm^3/g$, or even more preferably 0.4 to 0.5 $cm^3/g$, and an average pore diameter of 50 to 300 angstroms (Å), preferably 100 to 250 Å, or even more preferably 150 to 200 Å. In some embodiments, the active catalyst composition has a specific surface area in a range of 50 to 200 $m^2/g$, preferably 100 to 150 $m^2/g$, or even more preferably about 125 $m^2/g$. Other ranges are also possible.

The catalysts were characterized in terms of their textural properties, acidity, basicity, and surface reducibility, via Brunauer-Emmett-Teller (BET), $NH_3$-temperature programmed desorption ($NH_3$-TPD), $CO_2$-temperature programmed desorption $CO_2$-TPD, and $H_2$-temperature-programmed reduction ($H_2$-TPR) analysis. The coordination environments of the vanadium species were probed with diffuse reflectance UV-Vis spectra (UV-Vis DRS) and Raman spectroscopy. The catalysts were investigated for carbon dioxide mediated oxidative dehydrogenation ($CO_2$-ODH) of propane to propylene in a fixed-bed reactor.

As used herein, the term "temperature program reduction using $H_2$," or "$H_2$-TPR", generally refers to a technique used to study the reducibility of a solid material, such as an active catalyst composition, by measuring the consumption of a reducing gas, such as hydrogen, as a function of temperature. In some embodiments, the active catalyst composition is first heated in an oxidizing gas, such as air or oxygen, to remove any adsorbed species and to convert the active catalyst composition to an oxide. In some further embodiments, the active catalyst composition is then cooled down and exposed to a stream of hydrogen gas, while the temperature is gradually increased. As the temperature increases, the hydrogen reacts with the oxidized active catalyst composition, causing a reduction of the material. In some preferred embodiments, this reduction reaction may be exothermic, and the heat generated by the reaction is monitored as a function of temperature.

Figure 9A:
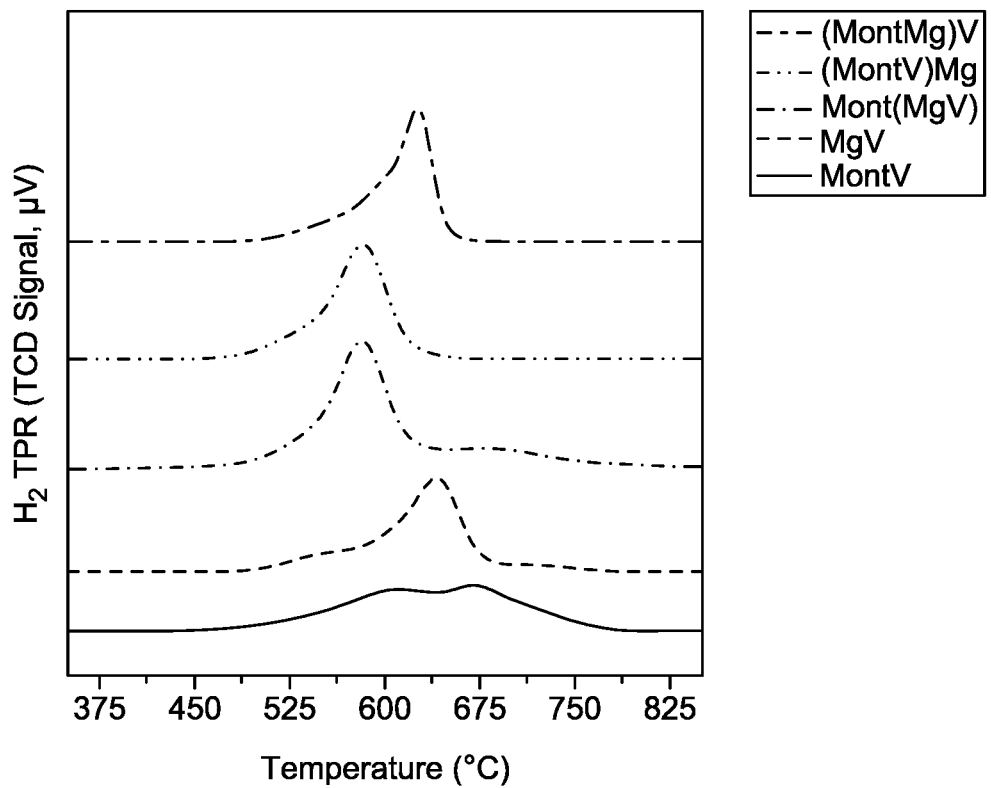
FIG. 9A shows an $H_2$ temperature programmed reduction ($H_2$-TPR) profile for various catalysts (MontV, MgV, (MontV)Mg, Mont(MgV) and (MontMg)V), according to certain embodiments.
Figure 9B:
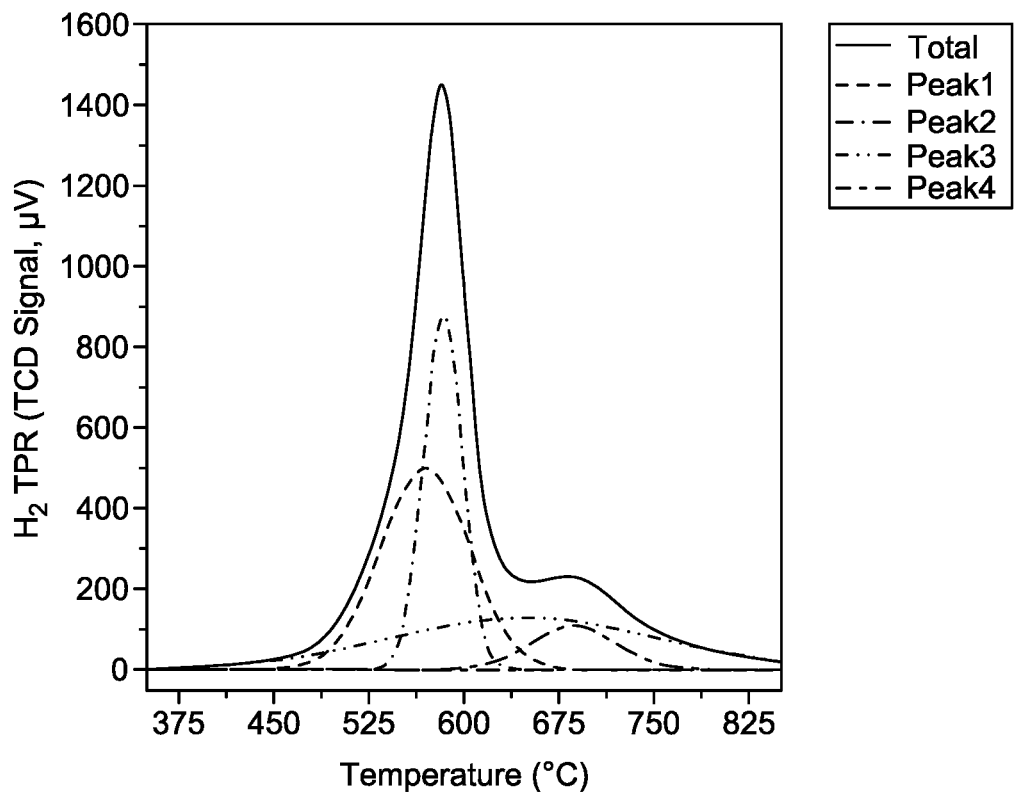
FIG. 9B shows a deconvoluted profile for the Mont(MgV) catalyst depicting various peaks, according to certain embodiments.

Referring to FIGS. 9A and 9B, hydrogen-temperature programmed reduction ($H_2$-TPR) plots of MontV, MgV, (MontV)Mg, Mont(MgV) and (MontMg)V catalyst. In some embodiments, the $H_2$-TPR was conducted on a Micromeritics AutoChem-II 2920 unit equipped with a TCD detector. The active catalyst was placed in a quartz calcined at a temperature of 200 to 400° C., preferably 225 to 375° C., preferably 250 to 350° C., preferably 275 to 325° C., or even more preferably about 300° C. under an argon flow for at least 60 minutes, at least 120 minutes, at least 180 minutes. In some further embodiments, the active catalyst was cooled to a temperature of no more than 70° C., preferably no more than 60° C., or even more preferably no more than 50° C. In some preferred embodiments, a gas flow contains hydrogen ($H_2$) and argon (Ar) in a volumetric ratio of $H_2$ to Ar ranging from 1:20 to 1:1, preferably 1:15 to 1:5, or even more preferably about 1:10 was introduced to flow over the active catalyst composition at a flow rate of 10 to 100 cubic centimeters per minutes ($cm^3$/min), preferably 30 to 70 $cm^3$/min, or even more preferably about 50 $cm^3$/min. In some preferred embodiments, the temperature of the analyzer containing the active catalyst was increased at ramping rate of 5 to 20° C. per minute until the temperature reaches about 900° C. Other ranges are also possible. In some most preferred embodiments, the composition of the present disclosure has an $H_2$-TPR in a range of 0.1 to 1 mmol/g, preferably 0.1 to 0.8 mmol/g, preferably 0.2 to 0.6 mmol/g, and more preferably to 0.3 to 0.4 mmol/g, as depicted in FIG. 9A. Other ranges are also possible.

As used herein, the term "$N_2$ adsorption/desorption method" generally refers to a technique used to measure the specific surface area of a solid material, such as a catalyst or a porous material. In some embodiments, the active catalyst composition is exposed to a stream of nitrogen gas at low temperature and pressure. The nitrogen gas is adsorbed onto the surface of the active catalyst composition, filling the pores and creating a monolayer of adsorbed nitrogen. In some further embodiments, the amount of nitrogen adsorbed at a given pressure is measured using a gas adsorption instrument, such as a BET instrument. In some preferred embodiments, the BET analysis is performed on a BELCAT II Chemisorption analyzer according to the software manual, manufactured by Bell Japan. In some more preferred embodiments, the nitrogen gas is gradually removed from the active catalyst composition, causing the desorption of the adsorbed nitrogen. The amount of nitrogen desorbed at a given pressure is also measured using the gas adsorption instrument. By analyzing the amount of nitrogen adsorbed and desorbed, the specific surface area of the active catalyst can be calculated using the BET (Brunauer-Emmett-Teller) and Barrett, Joyner and Halenda (BJH) equation.

Referring to FIGS. 4A to 4B, and 5A to 5C, $N_2$ adsorption-desorption isotherms of MontV, MgV, (MontV)Mg, Mont(MgV) and (MontMg)V catalyst. In some embodiments, the $N_2$-TPR was conducted on a Micromeritics ASAP 2020 sorption analyzer. In some embodiments, the active catalyst composition of the present disclosure has a total pore volume in a range of 0.1 to 1 $cm^2$/g, preferably 0.1 to 0.8 $cm^2$/g, preferably 0.2 to 0.6 $cm^2$/g, and more preferably to 0.3 to 0.4 $cm^2$/g, as depicted in FIGS. 4A to 4B, and 5A to 5C. Other ranges are also possible.

As used herein, the term "temperature program desorption using carbon dioxide," or "$CO_2$-TPD" generally refers to a technique used to study the surface acidity of a solid material, such as an active catalyst. In some embodiments, the active catalyst is first heated in an inert gas, such as nitrogen, to remove any adsorbed species and to stabilize the surface. In some embodiments, the active catalyst is then cooled down and exposed to a stream of carbon dioxide gas, which is adsorbed onto the surface of the active catalyst. The amount of carbon dioxide adsorbed is proportional to the surface acidity of the active catalyst. The active catalyst is then heated at a constant rate while the amount of carbon dioxide desorbed is monitored as a function of temperature. In some further embodiments, as the temperature increases, the adsorbed carbon dioxide begins to desorb from the surface of the active catalyst. In some preferred embodiments, the desorption of carbon dioxide may be exothermic, and the heat generated by the desorption process is monitored using a thermal conductivity detector.

Figure 11A:
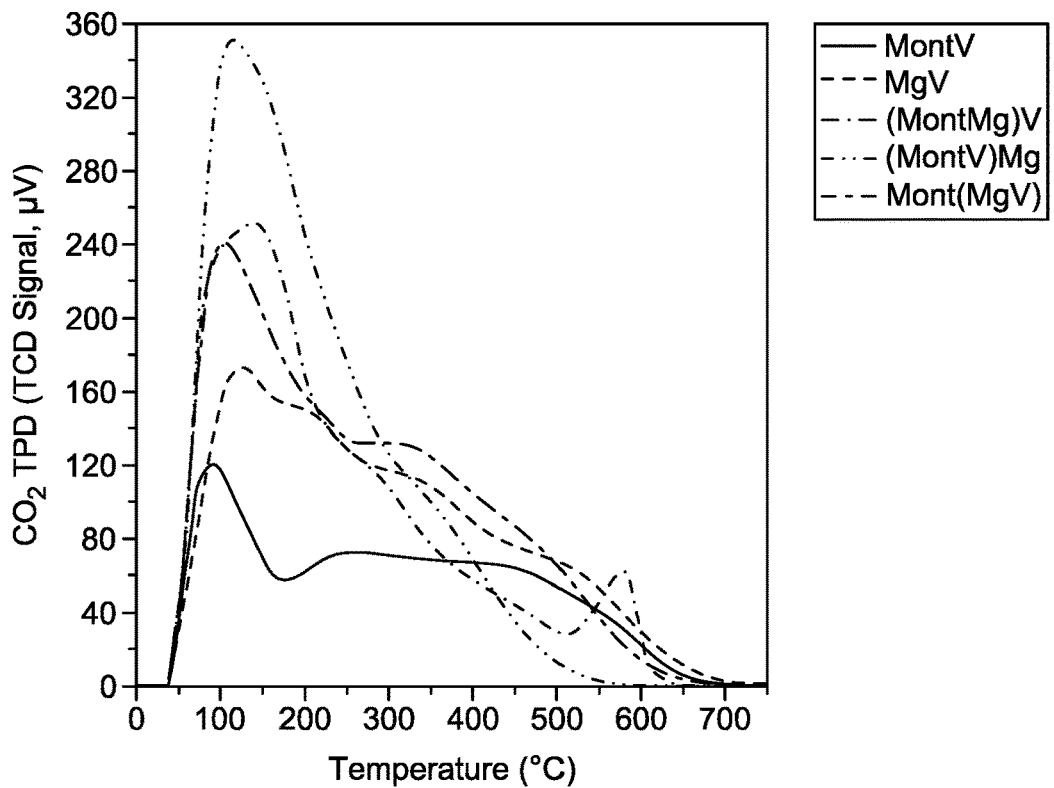
FIG. 11A shows a $CO_2$ temperature programmed desorption ($CO_2$-TPD) for the various catalysts, according to certain embodiments.
Figure 11B:
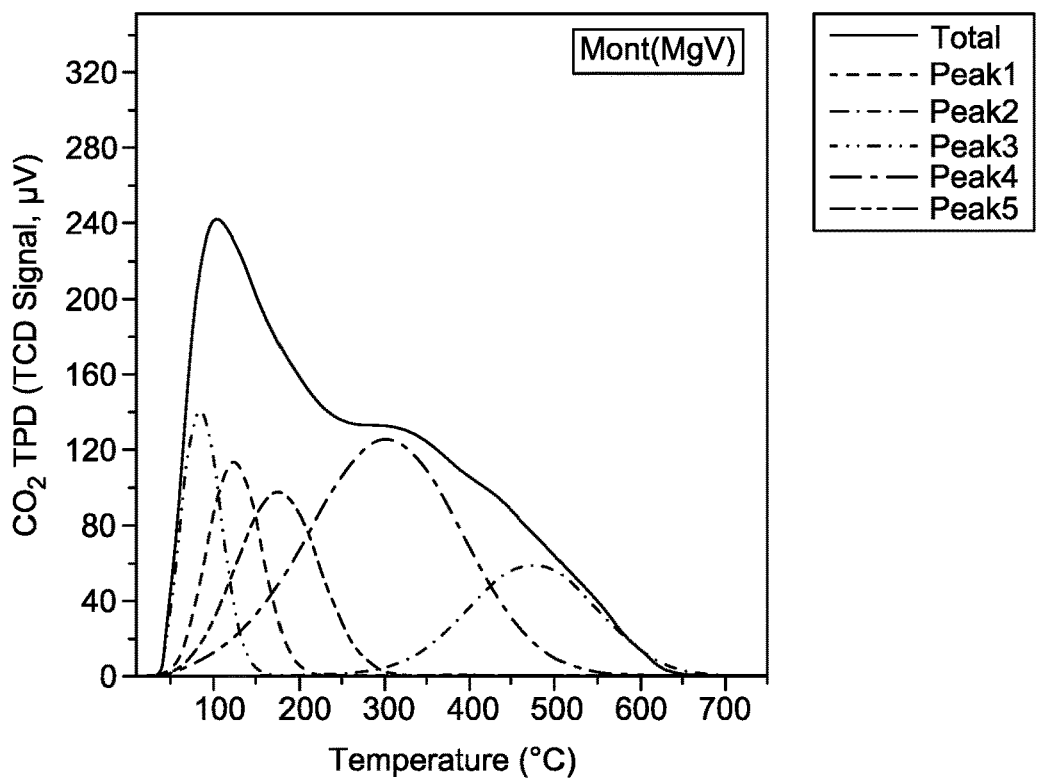
FIG. 11B shows a deconvoluted profile for the Mont (MgV) catalyst depicting various peaks, according to certain embodiments.

Referring to FIGS. 11A to 11B, $CO_2$ temperature programmed desorption ($CO_2$-TPD) of MontV, MgV, (MontV)Mg, Mont(MgV) and (MontMg)V catalyst. In some embodiments, the $CO_2$-TPD was conducted on a BELCAT II Chemisorption analyzer. In some embodiments, the active catalyst composition of the present disclosure has a total basicity in a range of 0.1 to 4 mmol/g, preferably 0.5 to 3 mmol/g, preferably 1 to 2 mmol/g, and more preferably to 1.2 to 1.5 mmol/g, as depicted in FIGS. 11A to 11B. Other ranges are also possible.

As used herein, the term "temperature program desorption using ammonia," or "$NH_3$-TPD" generally refers to a technique used to study the surface basicity of a solid material, such as an active catalyst. In some embodiments, the active catalyst is first heated in an inert gas, such as nitrogen, to remove any adsorbed species and to stabilize the surface. In some embodiments, the active catalyst is then cooled down and exposed to a stream of ammonia gas, which is adsorbed onto the surface of the active catalyst. The amount of ammonia adsorbed is proportional to the surface basicity of the active catalyst. In some embodiments, the active catalyst is then heated at a constant rate while the amount of ammonia desorbed is monitored as a function of temperature. In some further embodiments, ss the temperature increases, the adsorbed ammonia begins to desorb from the surface of the active catalyst. In some preferred embodiments, the desorption of ammonia may be exothermic, and the heat generated by the desorption process is monitored using a thermal conductivity detector.

Figure 10A:
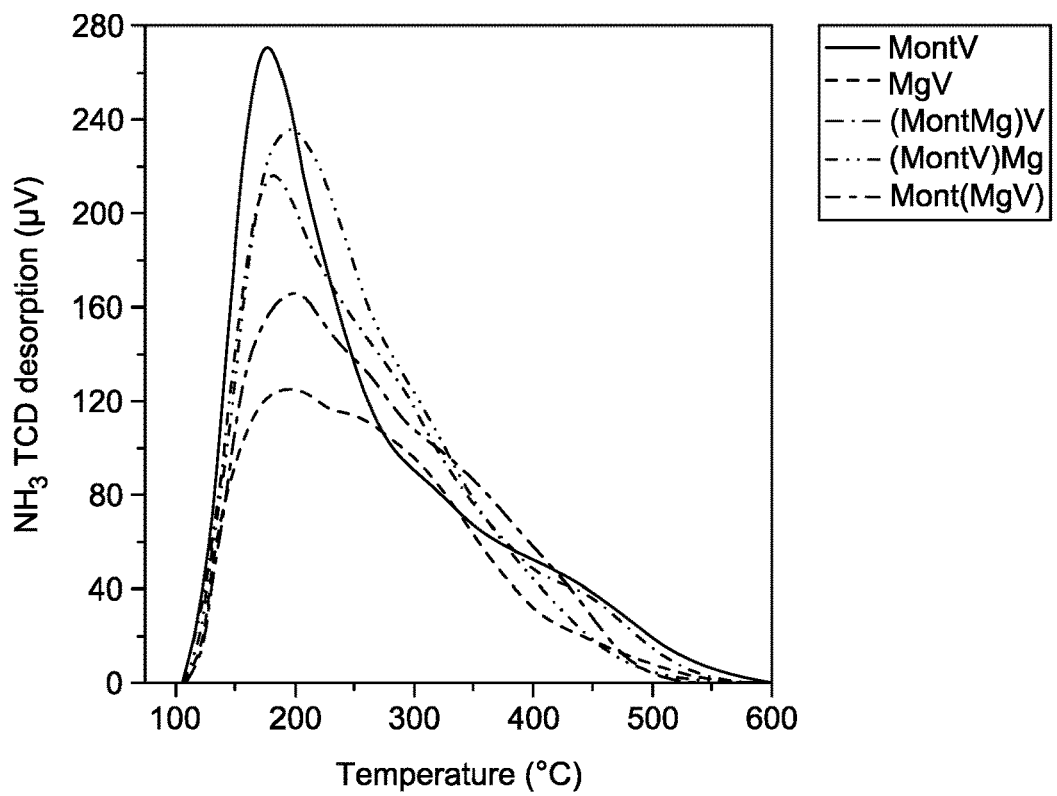
FIG. 10A shows the $NH_3$ temperature programmed desorption ($NH_3$-TPD) for the various catalysts, according to certain embodiments.
Figure 10B:
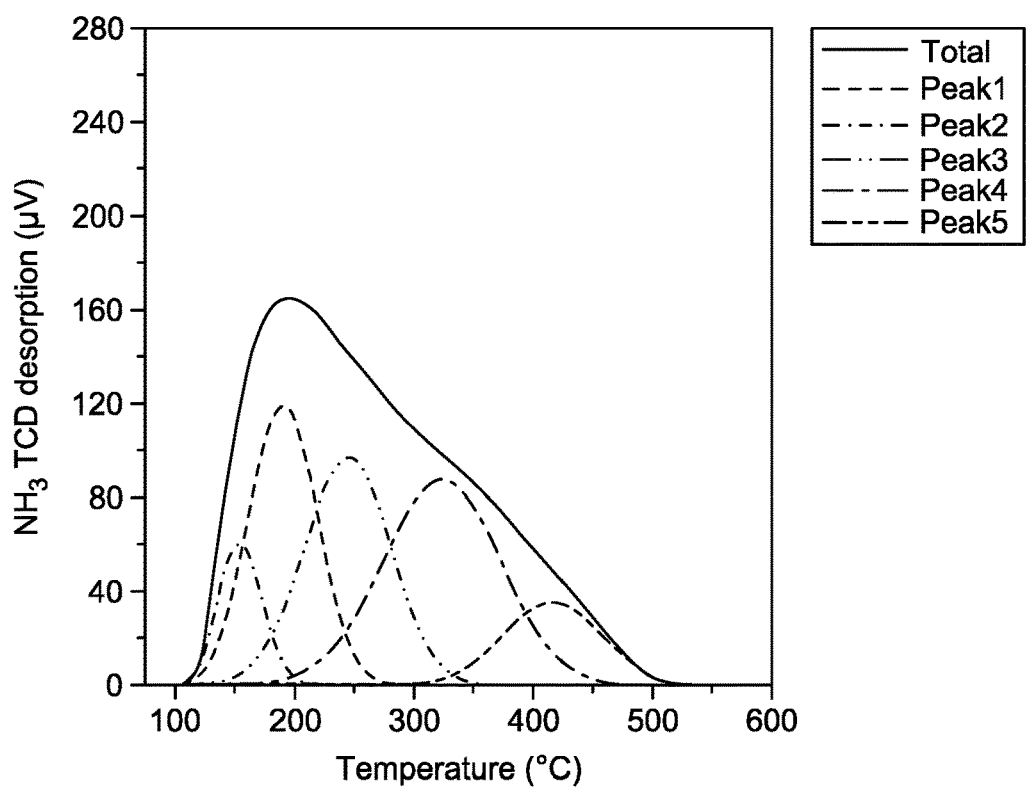
FIG. 10B shows a deconvoluted thermal conductivity detector (TCD) signal for the Mont(MgV) catalyst depicting various peaks, according to certain embodiments.

Referring to FIGS. 10A to 10B, $NH_3$ temperature programmed desorption ($NH_3$-TPD) of MontV, MgV, (MontV)Mg, Mont(MgV) and (MontMg)V catalyst. In some embodiments, the $NH_3$-TPD was conducted on a BELCAT II Chemisorption analyzer. In some embodiments, the active catalyst composition of the present disclosure has a total acidity in a range of 0.001 to 0.1 mmol/g, preferably 0.005 to 0.08 mmol/g, preferably 0.01 to 0.04 mmol/g, and more preferably about 0.02 mmol/g, as depicted in FIGS. 10A to 10B. Other ranges are also possible.

Figure 2B:
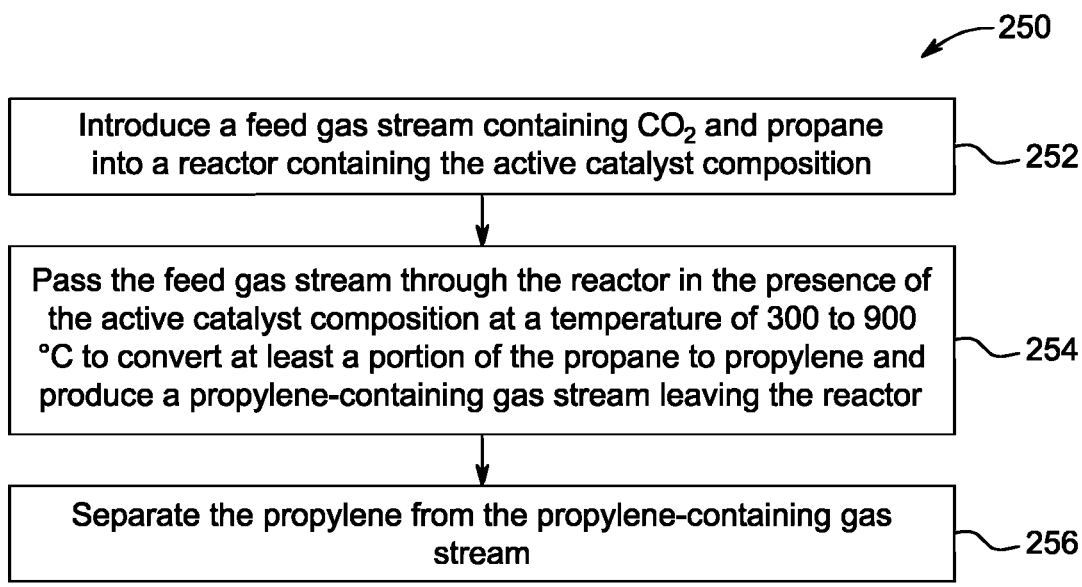
FIG. 2B is a schematic representation depicting a method for producing propylene via oxidative dehydrogenation (ODH) of propane, according to certain embodiments.

Referring to FIG. 2B, a schematic flow diagram of the method 250 for producing propylene via oxidative dehydrogenation of propane is illustrated. The order in which the method 250 is described is not intended to be construed as a limitation, and any number of the described method steps may be combined in any order to implement the method 250. Additionally, individual steps may be removed or skipped from the method 250 without departing from the spirit and scope of the present disclosure.

At step 252, the method 250 includes introducing a feed gas stream containing $CO_2$ and propane into a reactor containing the active catalyst composition. The volume ratio of $CO_2$ to propane in the feed gas stream is in a range of 1:10 to 10:1, preferably 1:1 to 5:1, and more preferably 1:1. The feed is a mixture of $CO_2$ and propane. Optionally, the feed may include other gases such as $O_2$, water vapor, nitrogen, or combinations thereof. The feed may also include promoters, such as carbon monoxide, nitrous oxide, $N_2O$, $H_2O_2$, $O_3$, and combinations thereof, to increase efficacy. The $CO_2$ and propane, optionally with other gases, are introduced into the reactor, as a mixture, through one or more inlets. In some embodiments, the reactor is at least one selected from the group consisting of a fixed-bed reactor, a trickle-bed reactor, a moving bed reactor, a rotating bed reactor, a fluidized bed reactor, and a slurry reactor. In an embodiment, the reactor is a fixed-bed reactor in the form of a vertical cylindrical reactor which includes a top portion, a vertically oriented cylindrical body portion, a bottom portion, a housing. In some embodiments, the housing has an open top, and open bottom supportably maintained with the vertically oriented cylindrical body portion. The active catalyst composition is supportably retained within the housing, permitting fluid flow therethrough. In some embodiments, the vertical cylindrical reactor further includes at least one propeller agitator disposed in the bottom portion of the reactor. In some embodiments, the main function of the propeller agitator is homogenization, dispersion, and suspension of low-viscosity products. In some embodiments, the bottom portion is cone-shaped or pyramidal. In an embodiment, the bottom portion may have a cylindrical, cubical, cuboidal, or rhombic shape. In some preferred embodiments, a plurality of recirculation tubes fluidly connects the bottom portion of the vertical cylindrical reactor with the vertically oriented cylindrical body portion of the vertical cylindrical reactor. In an embodiment, the fixed-bed reactor may be made up of a material such as stainless-steel, iron, aluminum, copper, lead, iron, zirconium, or another alloy.

At step 254, the method 250 includes passing the feed gas stream through the reactor in the presence of the active catalyst composition at a temperature of 300 to 900° C. to convert at least a portion of propane to propylene and produce a propylene-containing gas stream leaving the reactor. The pressure is maintained between 0.01 atm to 20 atmospheres. The conversion may be facilitated using UV, visible, or infrared light to promote the dehydrogenation reaction. The active catalyst composition converts at least a portion of propane to propylene. In some embodiments, the active catalyst composition converts at least 80% of propane to propylene based on the initial weight of the propane in the feed gas stream, preferably at least 90%, or even more preferably at least 99% based on the initial weight of the propane in the feed gas stream. The ODH reaction also results in a propylene-containing gas stream. The propylene-containing gas stream includes methane, ethane, ethylene, propane, carbon monoxide, carbon dioxide, a hydrocarbon containing $C_4$-$C_9$ such as butane, butene, pentane, and pentene; and aromatics such as benzene, naphthalene, anthracene, or their isomers, or mixtures of these substance. In some embodiments, the $C_4$-$C_9$ hydrocarbon contains butane, butene, butyne, pentane, pentene, pentyne, hexane, hexene, hexyne, cyclohexane, cyclohexene, heptane, heptene, heptyne, octane, octene, octyne, nonane, nonene, nonyne, or their isomers, or mixtures of these substance.

In some embodiments, the propylene is present in the propylene-containing gas stream at a concentration of 30 to 70 wt. %, more preferably 35 to 65 wt. %, preferably 40 to 60 wt. %, preferably 45 to 55 wt. %, each wt. % based on a total weight of the converted propane. In some embodiments, the ethylene is present in the propylene-containing gas stream at a concentration of to 30 wt. %, more preferably 10 to 25 wt. %, or even more preferably 15 to 20 wt. %, each wt. % based on a total weight of the converted propane. In some embodiments, the ethane is present in the propylene-containing gas stream at a concentration of 0.001 to 5 wt. %, more preferably 0.01 to 3 wt. %, or even more preferably 0.1 to 2 wt. %, each wt. % based on a total weight of the converted propane. In some embodiments, the methane is present in the propylene-containing gas stream at a concentration of 1 to 20 wt. %, more preferably 5 to 15 wt. %, or even more preferably about 10 wt. %, each wt. % based on a total weight of the converted propane. Other ranges are also possible.

At step 256, the method 250 separating the propylene from the propylene-containing gas stream. The unreacted propane (exiting from the propylene-containing gas stream) may be fed back into the reactor through the inlet for the ODH process. The method of the present disclosure yields up to 40% of propylene based on the propane conversion, preferably up to 35%, or even more preferably up to 30% of propylene based on the propane conversion.

In some embodiments, $VO_x$ supported on the montmorillonite (MontV) and magnesium oxide (MgV) exhibited moderate propylene yields (19.6 and 18.2%, respectively) but with high CO selectivity at 625° C. In some further embodiments, MgO-supported vanadium supported on montmorillonite (Mont(MgV)) developed via physical grinding of MgV with montmorillonite displayed outstanding catalytic performance, with around 31% yield to propylene without observable deactivation for 12 h TOS.

EXAMPLES

The following examples demonstrate the catalytic composition as described herein. The examples are provided solely for illustration and are not to be construed as limitations of the present disclosure, as many variations thereof are possible without departing from the spirit and scope of the present disclosure.

Example 1: Catalyst Synthesis

A series of supported vanadium-based catalysts were synthesized via solvent and template-free protocols. In a typical synthesis, 1.5 g of as-received montmorillonite (Acros organics, Janssen-Pharmaceuticalaan 3a, 2440 Geel, Belgium) were crushed and sieved to collect particles less than a 100-micron sieve. The sieved montmorillonite particles and 1.5 g MgO(Sigma Aldrich) were individually mixed in a mortar with vanadium metal (utilizing vanadium (III) acetylacetonate as a precursor) equivalent to 4 wt. % of the total mass of support. The mixtures were then thoroughly ground using a mortar and pestle before adding 5 g of ethanol. The mixtures were ground for 5 minutes, dried at 95° C., and calcined at 600° C. for 6 hours at a heating rate of 5° C./min. The samples were labeled MontV and MgV, respectively. Finally, the montmorillonite and MgO were spatially integrated to exploit possible synergistic catalytic effects to develop other supported vanadium catalysts.

Example 2: Synthesis of the Mont(MgV) Catalyst

Using the same procedure as mentioned in Example 1, the same amount of constituent active species, the MgV was developed. The realized MgV was mixed in a mortar and pestle with 1.5 g of montmorillonite and ground thoroughly before adding 5 g ethanol. The mixture was ground for 5 minutes, dried at 95° C., and calcined at 300° C. for 3 h at a heating rate of 5° C./min to obtain the Mont(MgV) catalyst.

Example 3: Synthesis of the (Mont)VMg Catalyst

The same step as mentioned in Example 2 was repeated. However, the vanadium metal was loaded on montmorillonite only before mixing it with MgO support (double calcination).

Example 4: Synthesis of the (MontMg)V Catalyst

Both supports were added together and adequately ground for 5 min. Later, the vanadium metal precursor was added and mixed thoroughly before adding ethanol, followed by 5 min grinding in a mortar. The sample was dried at 95° C. and calcined at 600° C. for 3 h at a heating rate of 5° C./min. Several techniques were deployed to probe the properties of fresh and spent catalysts to establish strong property-activity relationships.

Example 5: UV-Vis DRS

UV-Vis DRS were acquired for the fresh samples on UV-VIS & UV-VIS-NIR Systems—Carry 5000 (manufactured by Agilent Technologies, 5301 Stevens Creek Blvd Santa Clara, CA 95051, U.S.A) in the range 200-800 nm in powder form. No standards or references, such as MgO or $BaSO_4$, were utilized. This enables probing of the co-ordination environment of the vanadium species over the supports.

Example 6: $NH_3$-TPD

The surface acid-base properties of the catalysts were probed using $NH_3$-TPD on a BELCAT II Chemisorption analyzer (manufactured by Microtrac Inc, 215 Keystone Dr, Montgomeryville, Pennsylvania, 18936, U.S.A). 0.1 g of the catalyst sample was pre-heated at 500° C. for 60 minutes at a heating rate of 10° C./min. Next, the samples were cooled to 100° before ammonia adsorption for 30 minutes at 30 mL/min. Subsequently, the samples are flushed with helium and heated to 600° C. at 10° C./min. The signals were acquired using a TCD detector.

Example 7: $N_2$ Adsorption Isotherms $N_2$ adsorption analysis was conducted on a Micromeritics ASAP 2020 sorption analyzer (manufactured by Micromeritics, 4356 Communications Dr. Norcross, GA 30093-2901, U.S.A) to probe the textural properties of the catalysts. Typically, 100 mg of catalyst samples were degassed in a vacuum at 300° C. for 6 h before the measurement in a liquid $N_2$ bath at −195.86° C. The BET method was utilized to quantify the specific surface areas, while the t-plot method was used to measure the external surface area and the mesoporous-microporous volumes of the catalysts. The pore distributions were measured via the NLDFT method.

Example 8: Raman and TGA

Fresh and spent catalyst spectra were obtained using a Raman spectrometer at ambient temperature. The excitation source was a wavelength of 532 nm and at 25 mW. This enables the probing of the surface disorder on the catalysts via the D and G band (ID/IG) ratio. Again, the TGA of the spent samples was carried out to corroborate the Raman spectra results obtained regarding the extent of coke formation on the catalyst surface.

Example 9: $H_2$ Reducibility

The surface reducibility of the fresh catalysts was probed via $H_2$-TPR on Micromeritics AutoChem-II 2920 unit equipped with a TCD detector (manufactured by Micromeritics, 4356 Communications Dr. Norcross, GA 30093-2901, U.S.A). 100 mg of catalyst is preheated in a quartz tube to 300° C. under Ar flow regulated at 50 mL/min, and the temperature was maintained for 3 h. Before the temperature reduction analysis, the sample is cooled to room temperature. Subsequently, a mixture of Ar and 10% by volume $H_2$ was flown at the rate of 50 mL/min while linearly heating the sample at the rate of 10° C./min up to 850° C. The signal is recorded with calibrated TCD detector.

Example 10: $CO_2$-TPD

The basicity of the catalysts was probed using $CO_2$ temperature programmed desorption ($CO_2$-TPD) on a BELCAT II Chemisorption analyzer (manufactured by Microtrac Inc, 215 Keystone Dr, Montgomeryville, Pennsylvania, 18936, U.S.A). Typically, 0.1 g of the catalyst sample was pre-heated at 500° C. for 60 minutes at a heating rate of 10° C./min. Next, the samples were cooled to 45° C. before $CO_2$ adsorption for 30 minutes at the rate of 30 mL/min. Subsequently, the samples are flushed with helium and heated to 900° C. at 10° C./min. Finally, the signals were acquired using a TCD detector.

Example 11: Catalytic Performance

Before the catalytic testing, the catalyst samples were pelletized, crushed, and sieved with a 330-345 mesh. In a typical run, 0.1 g of catalyst particles are loaded into a quartz reactor without diluting with inert materials such as SiC. In addition, quartz wool was utilized to position the catalyst bed appropriately inside the reactor. The reactor model is the PID Microactivity-Effi reactor, a fully-automated reactor (manufactured by Micromeritics Inc, 4356 Communications Dr. Norcross, GA 30093-2901, U.S.A) connected to an online 7820A Agilent gas chromatograph equipped with HP-Plot-Q capillary column and both TCD and FID detectors (manufactured by Agilent Technologies, 5301 Stevens Creek Blvd Santa Clara, CA 95051. United States). All gaseous products were analyzed accordingly. The line connecting the reactors with the GC is constantly maintained at 120° C. to ensure that the water produced during the $CO_2$-ODHP does not condense inside. The flow into the reactor is regulated using the Bronkhorst mass flow meters (manufactured by Bronkhorst Instruments GmbH, Am Ziegelwerk 1, 85391 Allershausen, Germany). The loaded catalyst is usually pre-treated with air at a flow rate of 30 mL/min while the bed is ramped to 675° C. at 20° C./min. Subsequently, the reactor temperature is cooled to the desired temperature for the reaction. The gas is switched to helium and maintained for 30 minutes to flush the catalyst and prepare it for reaction. Later, the reactor is isolated by activating the bypass valve, and the feed (mixture of propane and $CO_2$ at a ratio of 1:1) is flown continuously. When the flow stabilizes (around 10 min), the reactor is opened while the GC valves are activated after 2 min. The GC records the full FID and TCD chromatogram every 10 minutes. The GC was carefully calibrated with a standard gas mixture previously. The feed conversion, selectivity, and yield to a particular product are defined by equations (3) and (4), respectively.

Propane conversion, $$X_{C_3H_8} = \frac{(n_{C_3H_8})_{in} - (n_{C_3H_8})_{out}}{(n_{C_3H_8})_{in}} \times 100\% \quad (1)$$

$CO_2$ conversion, $$X_{C_3H_8} = \frac{(CO_2)_{in} - (CO_2)_{out}}{(CO_2)_{in}} \times 100\% \quad (2)$$

Hydrocarbons selectivity, $$S_i = \frac{z_j n_j}{3\left(n_{C_3H_{8_{in}}} - n_{C_3H_{8_{out}}}\right)} \times 100\% \quad (3)$$

CO selectivity, $$S_i = \frac{0.5 * (n_{CO} - n_{H_2O})}{3\left(n_{C_3H_{8_{in}}} - n_{C_3H_{8_{out}}}\right)} \times 100\% \quad (4)$$

Product yield, $Y_i = (X_{C_3H_8} * S_i) \times 100\%$ (5)

where $(n_{C_3H_8})_{in}$ and $(n_{C_3H_8})_{out}$ denote the inlet and outlet moles of the propane feed, while $z_j$ and $n_j$ denotes the number of carbons and moles of particular product species j.

Example 12: Catalyst Characterization

TABLE 1A

Textural, acidity, and surface reducibility properties for the catalysts

| | $N_2$ adsorption/desorption | | | | |
|---|---|---|---|---|---|
| Catalysts | $S_{BET}$ (m²/g · cat) | Smicro (m²/g · cat) | Total pore volume (cm²/g · cat) | Mesopore volume (cm²/g · cat) | Average pore volume |
| MgV | 84.0 | 5.6 | 0.49704 | 0.49450 | 220.8 |
| MontV | 160.5 | 5.5 | 0.33314 | 0.29674 | 81.9 |
| Mont(MgV) | 141.0 | 14.3 | 0.37423 | 0.36753 | 130.6 |

TABLE 1A-continued

Textural, acidity, and surface reducibility properties for the catalysts

| | $N_2$ adsorption/desorption | | | | |
|---|---|---|---|---|---|
| Catalysts | $S_{BET}$ (m²/g · cat) | Smicro (m²/g · cat) | Total pore volume (cm²/g · cat) | Mesopore volume (cm²/g · cat) | Average pore volume |
| (MontV)Mg | 71.1 | 3.5 | 0.32274 | 0.32255 | 196.6 |
| (MontMg)V | 110.7 | 11.1 | 0.28757 | 0.28288 | 95.6 |

TABLE 2B

Textural, acidity and surface reducibility properties for the catalysts

| Catalysts | $NH_3$-TPD Total acidity (mmol/g) | $CO_2$-TPD Total basicity (mmol/g) | $H_2$-TPR Surface reducibility (mmol/g $H_2$) |
|---|---|---|---|
| MgV | 84.0 | 5.6 | 0.49704 |
| MontV | 160.5 | 5.5 | 0.33314 |
| Mont(MgV) | 141.0 | 14.3 | 0.37423 |
| (MontV)Mg | 71.1 | 3.5 | 0.32274 |
| (MontMg)V | 110.7 | 11.1 | 0.28757 |

Example 13: Textural Properties

Figure 4A:
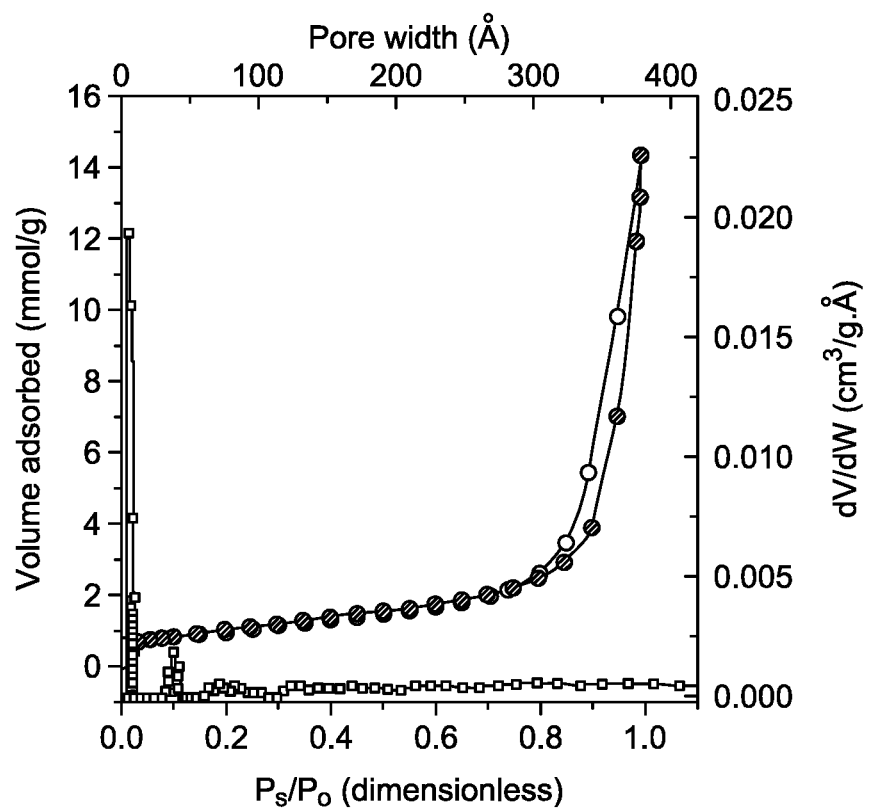
FIG. 4A is a plot depicting $N_2$ adsorption-desorption isotherms of a MgO supported vanadium (MgV) catalyst (fresh), according to certain embodiments.
Figure 4B:
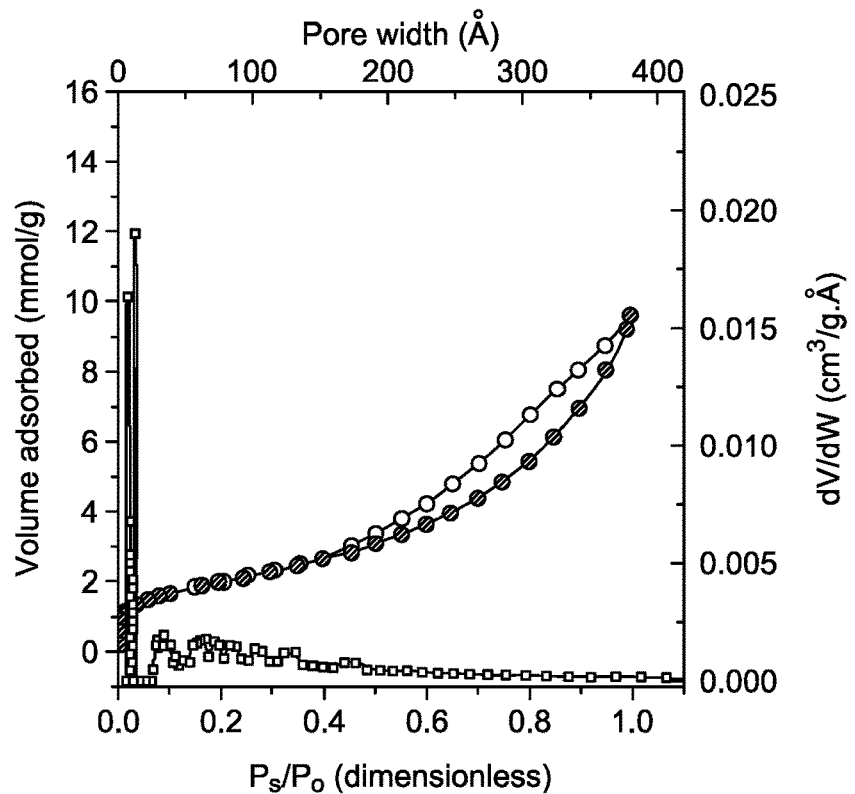
FIG. 4B is a plot depicting $N_2$ adsorption-desorption isotherms of a montmorillonite supported vanadium (MontV) catalyst (fresh), according to certain embodiments.
Figure 5A:
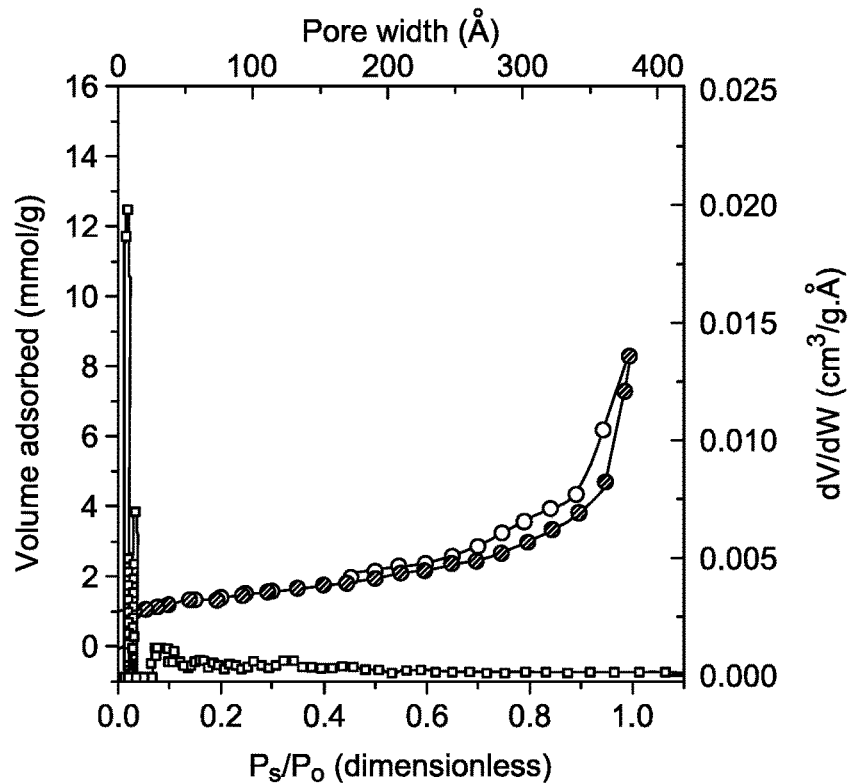
FIG. 5A is a plot depicting $N_2$ adsorption-desorption isotherms and non-linear density functional theory (NLDFT) pore size distribution of the MgV catalyst (fresh), according to certain embodiments.
Figure 5B:
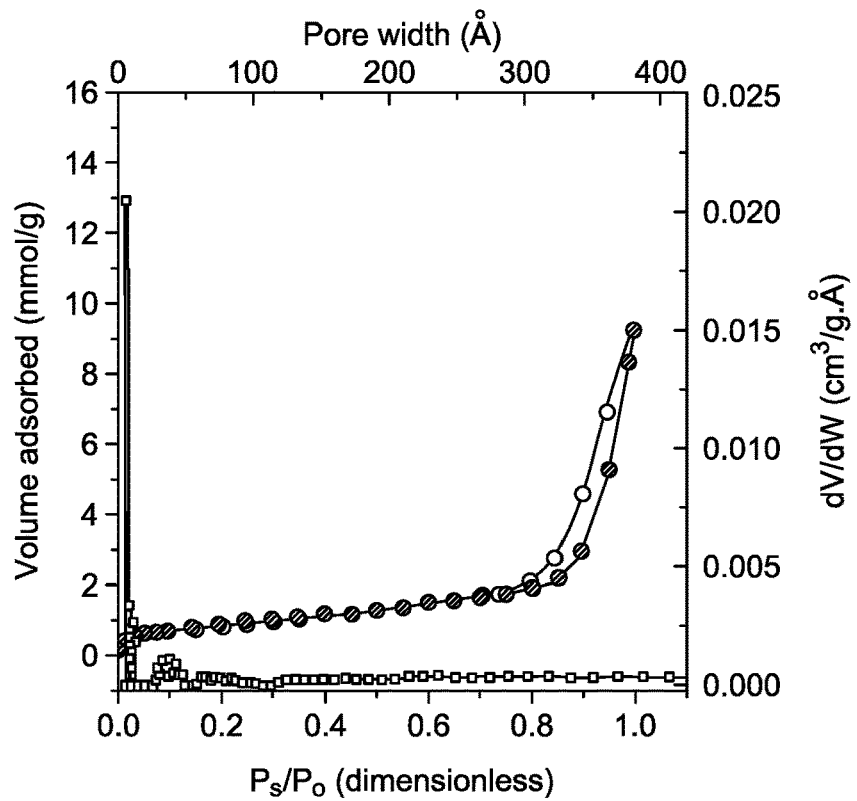
FIG. 5B is a plot depicting $N_2$ adsorption-desorption isotherms and NLDFT pore size distribution of the MontV catalyst (fresh), according to certain embodiments.
Figure 5C:
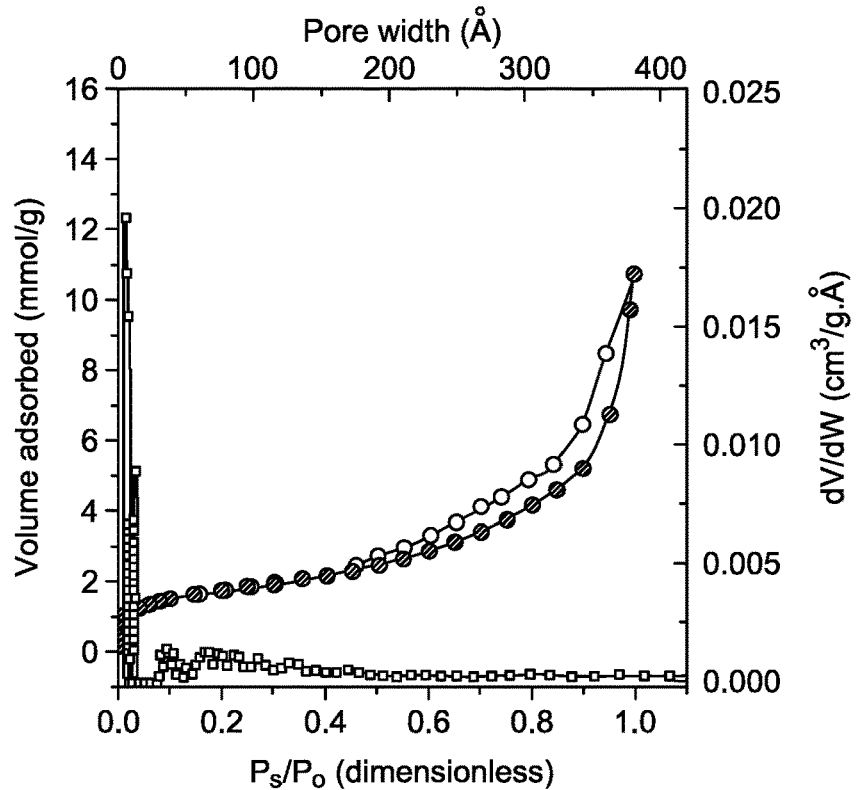
FIG. 5C is a plot depicting $N_2$ adsorption-desorption isotherms and NLDFT pore size distribution of a MontMg (V) fresh catalyst, according to certain embodiments.

FIG. 4A-FIG. 4B depict the $N_2$ adsorption-desorption isotherms of the MgV catalyst and the MontV catalyst, respectively. The NLDFT pore size distribution of the MgV, MontV, and MontMg(V) catalysts are depicted in FIG. 5A-5C. All the catalysts exhibited Type 4 isotherms with H1 hysteresis loops, typical of mesoporous materials. The pore diameter of the catalysts majorly falls in the range of 4.86-448.83 Å and 5.23-342 Å, respectively. As depicted in Table 1A, the MgV catalyst possesses the largest mesopores among all the samples. It has the largest average pore diameter of 220.8 Å while MontV exhibited the lowest 81.9 Å. However, MontV possesses the largest surface area of 160.5 m²/g·cat among all the catalysts (Table 1A).

The textural properties of the integrated catalysts appeared significantly modulated, and their values were strongly determined by those of the individual supports. Typically, incorporating Mont to construct Mont(MgV) improved the surface area of the catalyst to a magnitude 141.0 m²/g·cat, a value far above that of MgV (84.0 m²/g·cat). Similarly, the Mont(MgV) catalyst befitted from a large amount of mesopores and the large average pore diameter of the parent MgV. Thus, the integrated catalysts exhibited most of their textural properties as rough averages of MontV and MgV. Such modulation in the textural features of the integrated catalysts endow them with catalytic performances that are quite different from those of MontV and MgV.

Example 14: UV-Vis DRS

Figure 6A:
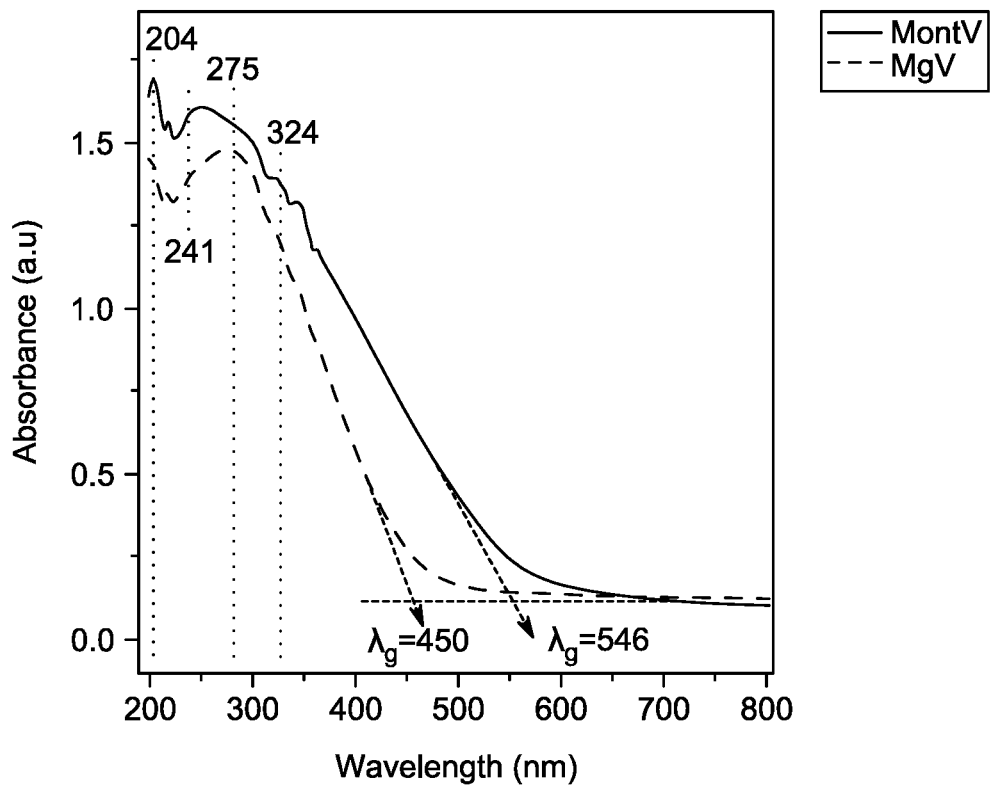
FIG. 6A shows a diffuse reflectance UV-Vis spectra (UV-vis DRS) absorbance versus wavelength (200-800 nm) plot for the MontV and the MgV catalysts, according to certain embodiments.
Figure 6B:
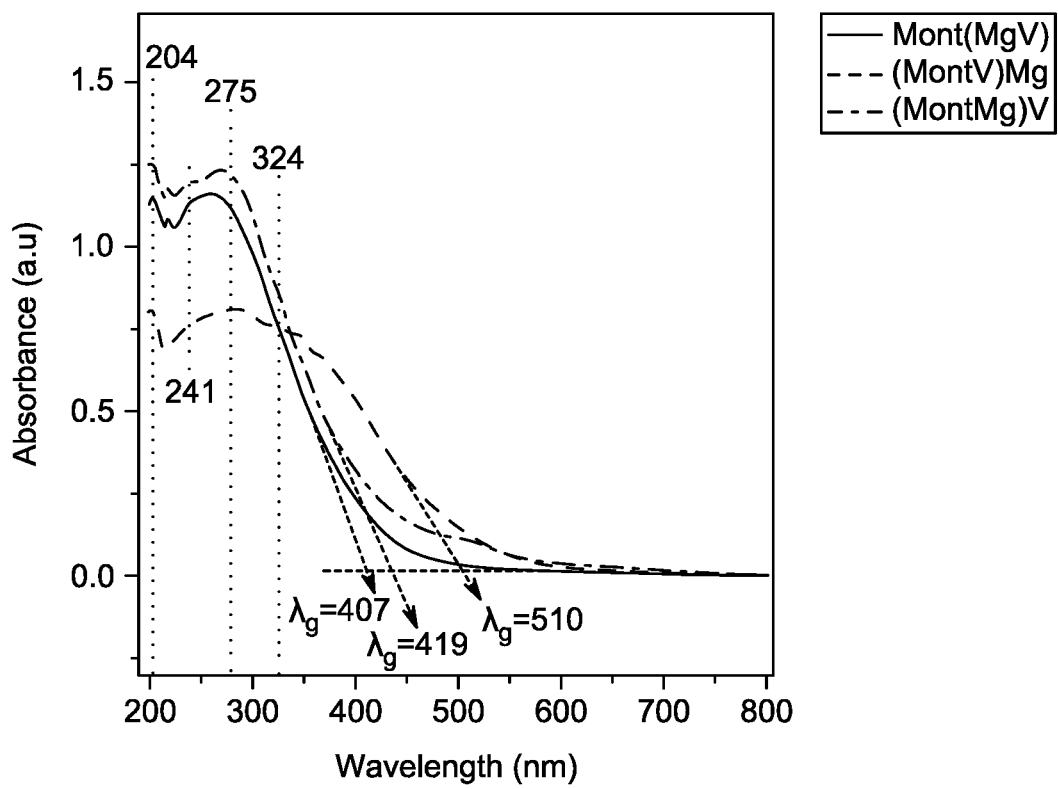
FIG. 6B shows a UV-vis DRS absorbance versus wavelength (200-800 nm) plot for the Mont(MgV), (MontV)Mg, and (MontMg)V catalysts at an absorbance versus wavelength (200-800 nm), according to certain embodiments.

The changes in the coordination environment of the vanadium species ($VO_x$) over the surface of the catalysts were probed via UV-vis DRS at ambient temperature. FIG. 6A depicts absorbance versus wavelength (200-800 nm) for all the catalysts. The spectra of MontV and MgV showed a band at 241 nm, corresponding to isolated $VO_x$ species (FIG. 6A). However, additional bands at 275, and 324 nm can be observed and are attributed to ligand-to-metal charge transfer (LMCT, $O^{2-} \rightarrow V^{5+}$), majorly in isolated and less polymerized $VO_x$ species. The presence of low-lying empty orbitals in the vanadium metal species enables the LMCT charge transfer. Moreover, the broadening and significant shifting of the electronic absorption bands of the MontV catalyst, especially between 350-500 nm, indicates that its surface $VO_x$ species are less dispersed. The bands above 500 nm depicted only on the MontV spectrum reveal more polymeric vanadia on the catalyst. Similarly, the spectra of the integrated catalysts, as illustrated in FIG. 6B, shows the presence of the same 241, 275, and 324 nm absorption bands; however, with lower intensities than those of the MontV and MgV catalysts.

Figure 7A:
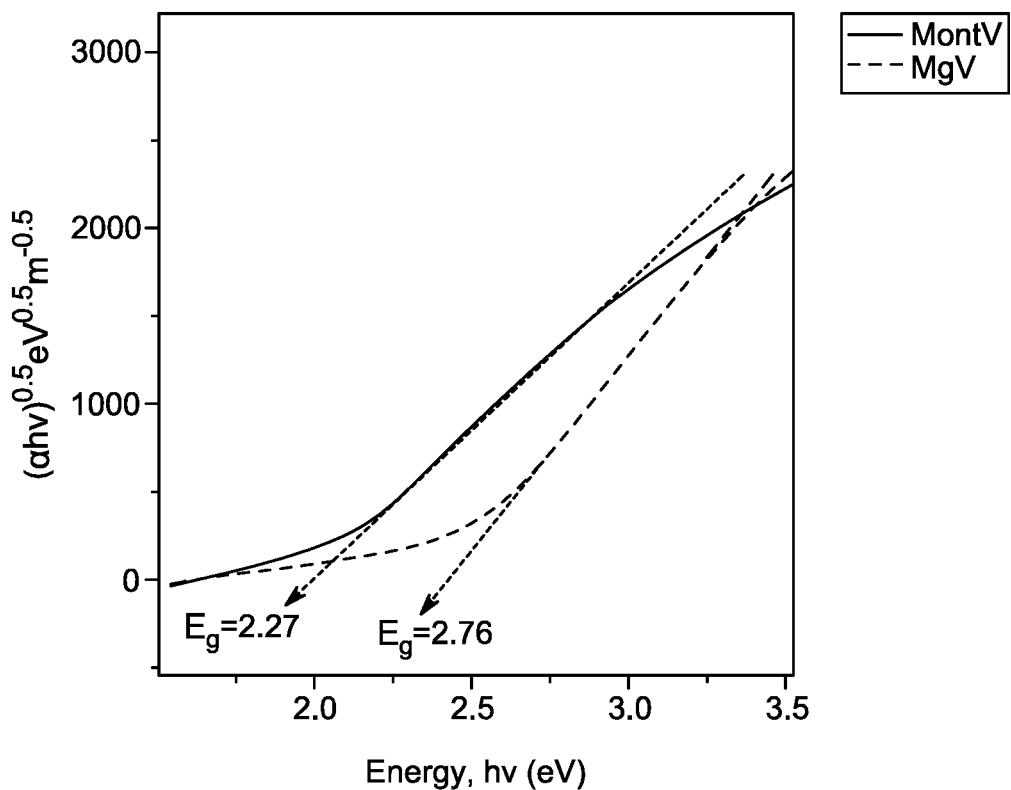
FIG. 7A is a plot of $(\alpha h v)^2$ versus incident photoenergy for band gap evaluation of the MontV and MgV catalysts, according to certain embodiments.
Figure 7B:
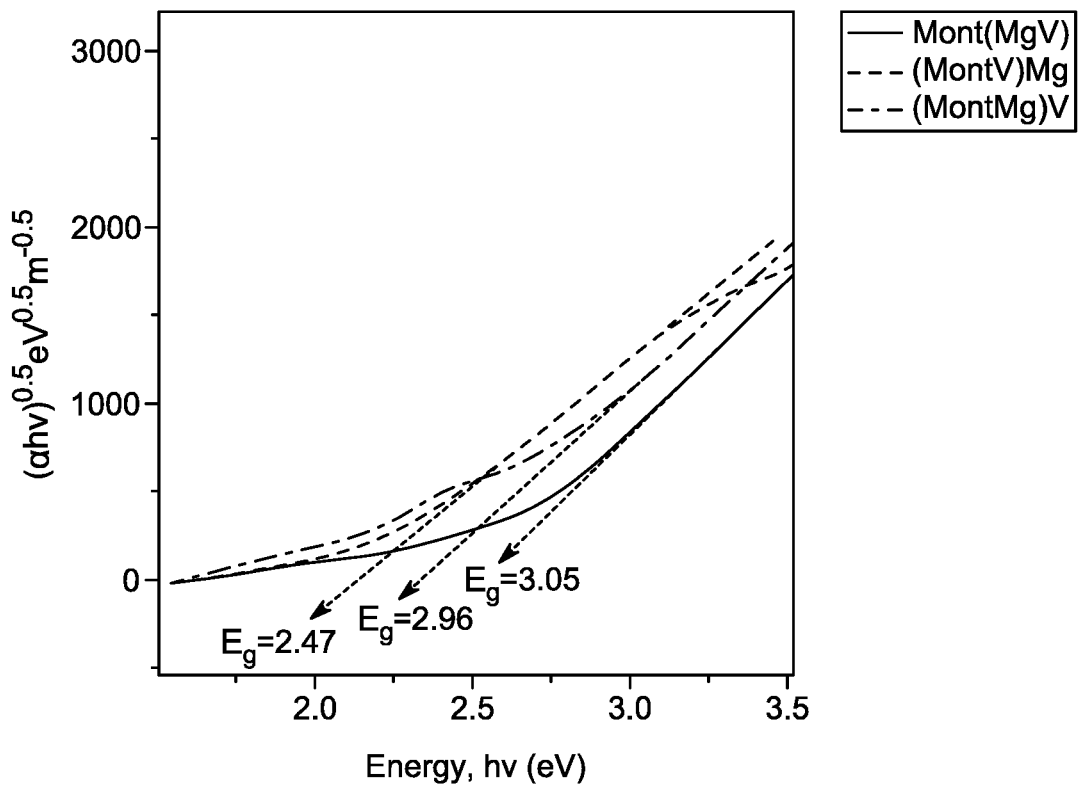
FIG. 7B is a plot of $(\alpha h v)^2$ versus incident photoenergy for band gap evaluation of the Mont(MgV), (MontV)Mg & (MontMg)V catalysts, according to certain embodiments.

This implies that the $VO_x$ phase is likely more dispersed on the integrated catalysts. To corroborate this, the energy band gaps of all the catalysts were evaluated, as depicted in FIG. 7A and FIG. 7B. Accordingly, the energy band gaps of the catalysts increase in the order MontV<(MontV)Mg<MgV<(MontMg)V<Mont(MgV). The significantly large band gap of Mont(MgV) reveals that it possesses the highest amount of less polymerized $VO_x$ species. This may cause a significant difference in its catalytic performance relative to the other samples.

Example 15: Raman Spectroscopy

Figure 8:
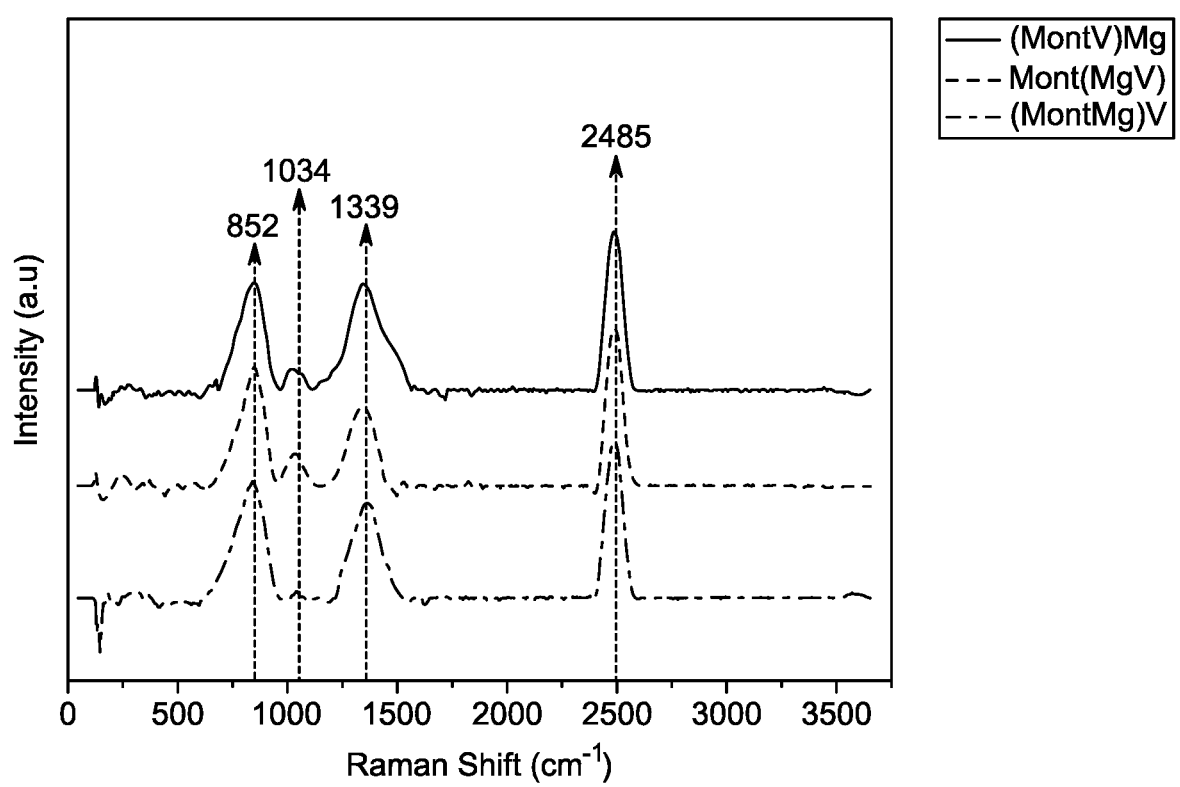
FIG. 8 is a Raman spectrum of the (MontV)Mg, Mont (MgV), and (MontMg)V integrated catalysts (fresh), according to certain embodiments.

To further investigate the nature of $VO_x$ species that evolved on the integrated catalysts, Raman spectra of the fresh catalysts were acquired. Raman spectroscopy is a powerful technique that can furnish vital insights into the surface chemistry of available active sites on heterogeneous metal oxide catalysts. FIG. 8 shows that all the spectra showed sharp absorption bands at 852, 1034, and 1339 $cm^{-1}$. The slight broadband at 852 $cm^{-1}$ relates to anti-symmetric stretching modes of bridging V-O-V bonds. Their symmetric counterparts were undetected because they should appear at around 500 cm'. Moreover, bands at 950 $cm^{-1}$ attributed to the crystalline $V_{2O5}$ phase were not observed for all the spectra. The band at 2485 $cm^{-1}$ appeared unchanged in all the spectra, probably due to residual organic impurities from the montmorillonite. Notably, the band at 1034 nm was attributed to the V=O stretching mode of surface $VO_x$ species and was broader on the (MontV)Mg spectra. This corroborated the observation in UV-vis DRS spectroscopy, where the Mont(MgV) catalyst exhibited the least polymerized $VO_x$ species, as evident from its highest band gap energy (3.05 eV).

Example 16: Surface Reducibility

FIG. 9A-FIG. 9B depict the $H_2$-TPR profile of all the catalysts. From FIG. 9A, the profiles reveal significant variation in the surface reducibility of the active phases of the catalysts. Typically, MontV exhibited higher reducibility than MgV, as depicted in Table 1B. This shows that variation in the nature of the support material can significantly influence the surface oxygen mobility of catalysts. It can be recalled that MontV gave the highest CO selectivity, which may partly be related to the high concentration of acid sites, less amount of mesopores, and high catalyst reducibility. From Table 1B, the trend in surface reducibility of the integrated catalyst follows the order (MontMg)V<Mont (MgV)<(MontMg)V, and that may be related to the variation in the coordination environment of the $VO_x$ species. For all the integrated catalysts, their reduction peaks shift to lower temperature ranges significantly. FIG. 9B depicted the deconvoluted profile of the Mont(MgV) catalysts showing 4 peaks. Notably, the catalyst exhibits reducible sites in the range 470-637° C. and a small amount of strong sites in the range 635-752° C. This feature may endow the catalyst to exercise significant kinetic control over the $CO_2$-ODH reaction within a wider temperature window.

Example 17: $NH_3$-TPD

The surface acidity of the catalysts was probed via $NH_3$-TPD analysis. From FIG. 10A and FIG. 10B, the $NH_3$-TPD profiles indicate that the desorption occurred between 100 and 590° C., signifying the presence of both medium and strong acid sites. According to Table 1B, the total amount of acid sites follows the trend MgV<Mont (MgV)<(MontV)Mg=(MontMg)V=MontV. The presence of MgO as a basic oxide would contribute to lowering the surface acidity of the catalysts. High concentration of acid sites, especially strong ones, can promote cracking and overoxidation as undesired pathways.

Example 18: $CO_2$-TPD

The concentration and nature of basic sites over the surfaces of the catalysts were probed via $CO_2$-TPD. From FIG. 11A-FIG. 11B, the $CO_2$-TPD profiles show that the desorption occurred between 45 and 650° C., revealing the presence of weak, medium, and strong basic sites over the catalysts. Furthermore, the intensity of the peaks varied significantly, indicating that the concentration of the sites was different in all the catalysts. According to Table 1B, the trend in the total amount of basic sites is in the order (MontMg)V>Mont(MgV)>MgV>(MontV)Mg>MontV.
Since the catalysts would be investigated for $CO_2$-mediated ODH reaction, a good amount of acid and basic site would favorably promote the surface coverage of $CO_2$ species from the gas phase that may probably enhance the rate of the reverse water-gas-shift reaction (RWGS) and, ultimately the overall $CO_2$-ODH catalytic performance via shifting the reaction equilibrium (in the case of two-step $CO_2$-ODH route majorly). Moreover, it may promote the reoxidation of the surface oxygen vacancy to restore the lattice oxygen site of the catalyst. Therefore, an efficient $CO_2$-ODH catalyst must have a balanced amount of acid and a basic site. The Mont(MgV) can be anticipated to exhibit good $CO_2$-ODH catalytic performance. FIG. 11B shows a deconvoluted Mont(MgV) catalyst profile depicting the various peaks.

Example 19: Catalytic Performance

Table 2 depicts the results of catalytic performances of the MgV and MontV catalysts for the $CO_2$-ODH of propane. For all the catalysts, as temperature increases, propylene selectivity, and propane conversion showed negative and positive trends, respectively. At a low temperature of 575° C., the MgV exhibited nearly double the propane and $CO_2$ conversions of the MontV sample. The MontV showed superior propylene selectivity at all temperatures, while MgV exhibited excellent catalytic activity. Moreover, the CO selectivity of the MontV catalyst was slightly higher. Catalysts with a higher concentration of acid sites would be expected to be less selective. However, the presence of MgO as a basic material in the MgV sample is likely to cause a significant reduction in the sample's acidity. So, the observed selectivity trends of the MontV and MgV samples may not be directly related to variation in acid properties. The variation in the catalytic behaviors of the sample could be exploited to rationally engineer potential catalysts by integrating the montmorillonite and MgO support.

TABLE 3

Catalytic performance for CO$_2$-mediated ODH of propane

| Catalysts | Temp (° C.) | Conversion (%) | | Product selectivity (%) | | | | | | Yield (%) |
|---|---|---|---|---|---|---|---|---|---|---|
| | | CO$_2$ | C$_3$H$_8$ | CO | CH$_4$ | C$_2$H$_6$ | C$_2$H$_4$ | C$_3$H$_6$ | Olefins | C$_3$H$_6$ |
| MgV | 575 | 15.6 | 28.7 | 26.9 | 6.5 | 0.0 | 13.1 | 53.5 | 66.6 | 15.4 |
| | 600 | 17.8 | 34.0 | 34.4 | 9.4 | 2.4 | 20.9 | 32.9 | 53.9 | 11.2 |
| | 625 | 23.8 | 52.0 | 35.3 | 8.3 | 1.5 | 17.3 | 37.6 | 55.0 | 19.6 |
| MontV | 575 | 7.1 | 15.2 | 29.4 | 3.0 | 0.0 | 11.7 | 55.8 | 67.6 | 8.5 |
| | 600 | 15.3 | 33.5 | 36.4 | 5.3 | 0.0 | 10.7 | 47.6 | 58.3 | 15.9 |
| | 625 | 18.0 | 44.6 | 37.3 | 7.1 | 0.0 | 14.8 | 40.8 | 55.5 | 18.2 |

Figure 12A:
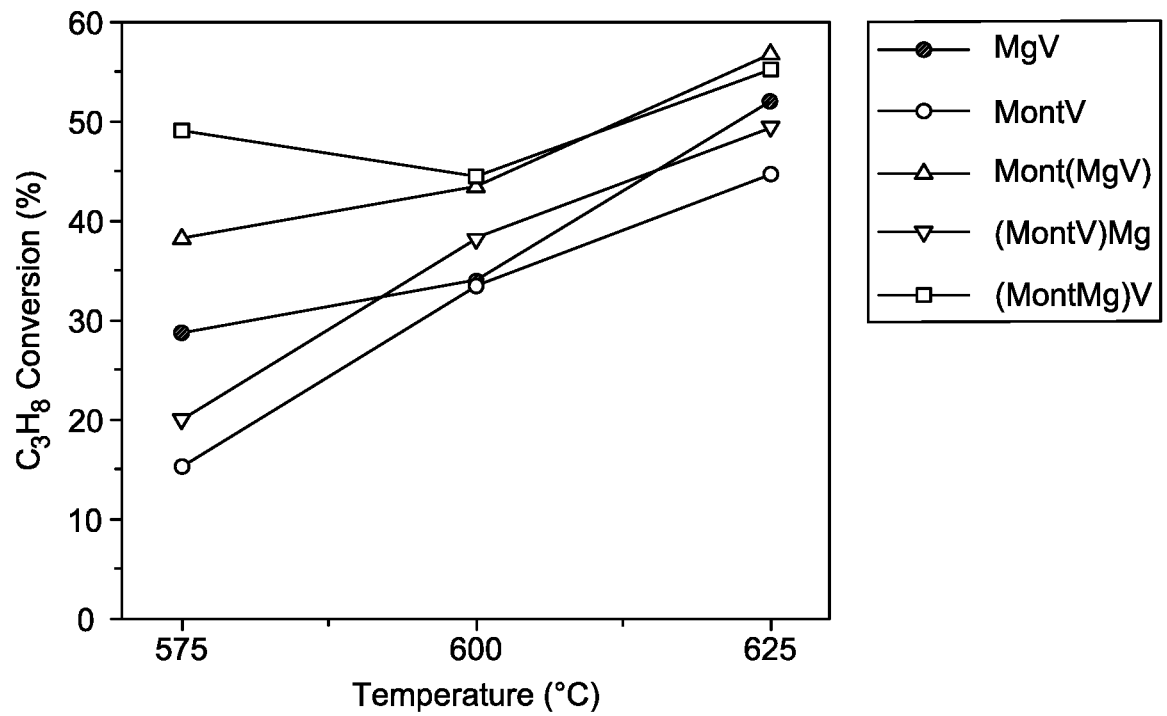
FIG. 12A is a plot of propane conversion depicting variation in the catalytic performance of the various catalysts with temperature, according to certain embodiments.
Figure 12B:
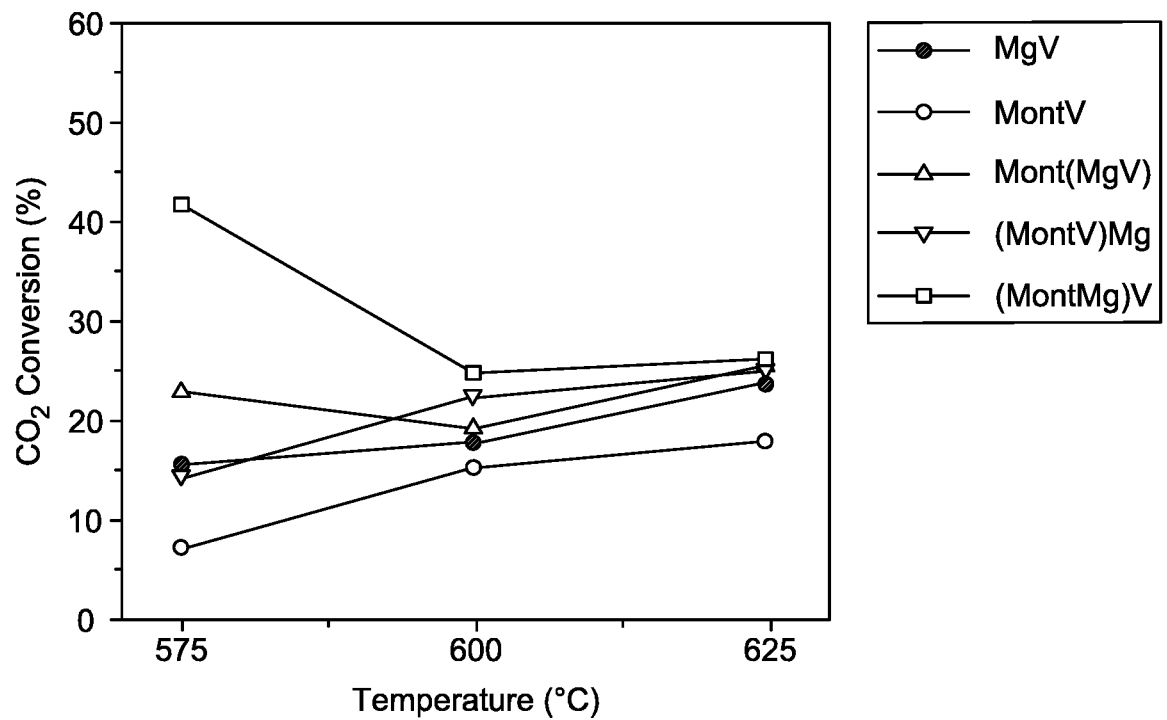
FIG. 12B is a plot of $CO_2$ conversion depicting variation in the catalytic performance of the various catalysts with temperature, according to certain embodiments.
Figure 12C:
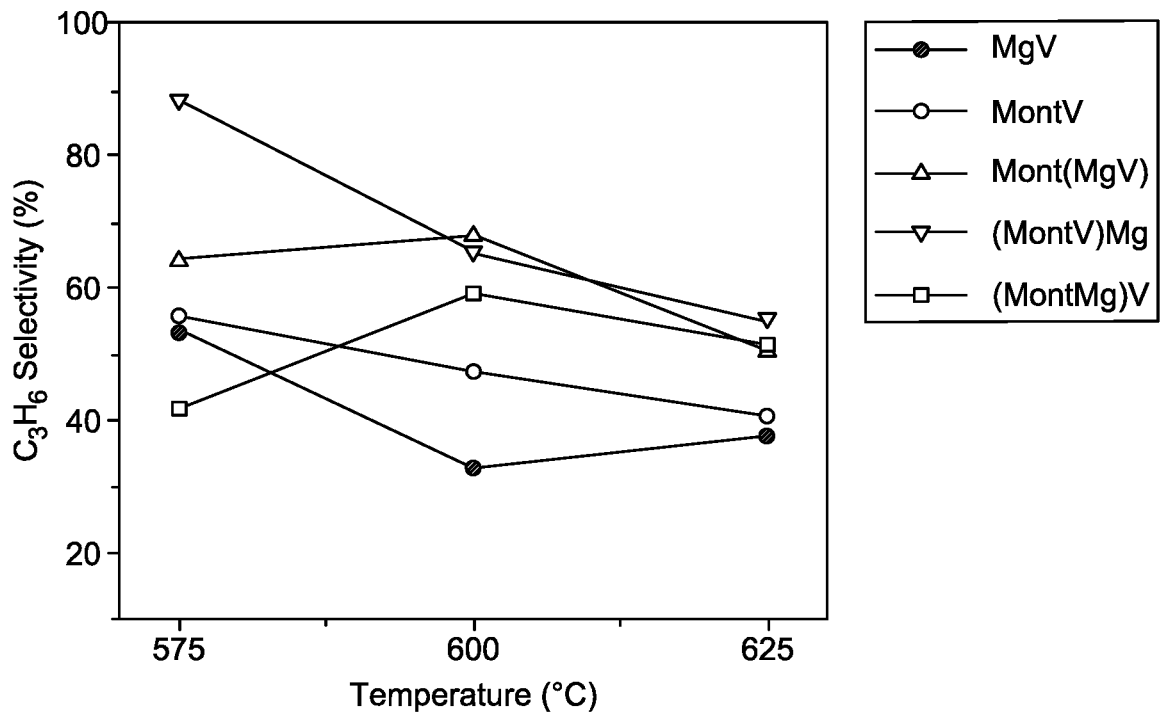
FIG. 12C is a plot of propylene selectivity depicting variation in the catalytic performance of the various catalysts with temperature, according to certain embodiments.
Figure 12D:
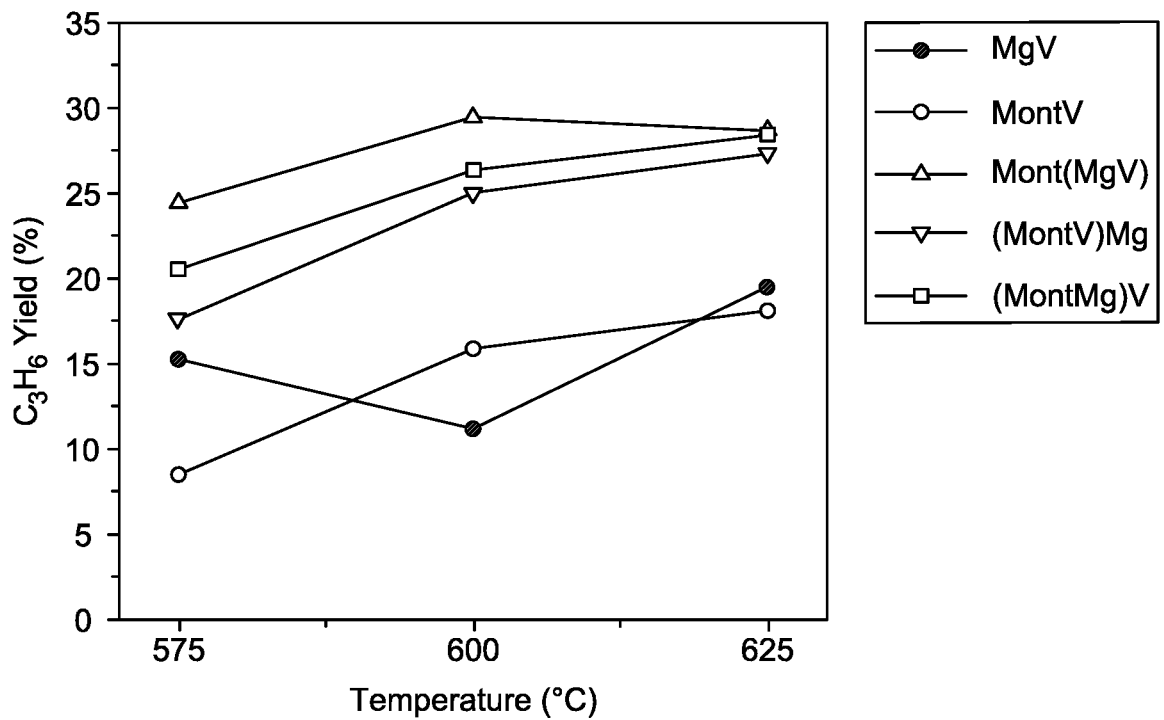
FIG. 12D is a plot of propylene yield depicting variation in the catalytic performance of the various catalysts with temperature, according to certain embodiments.
Figure 12E:
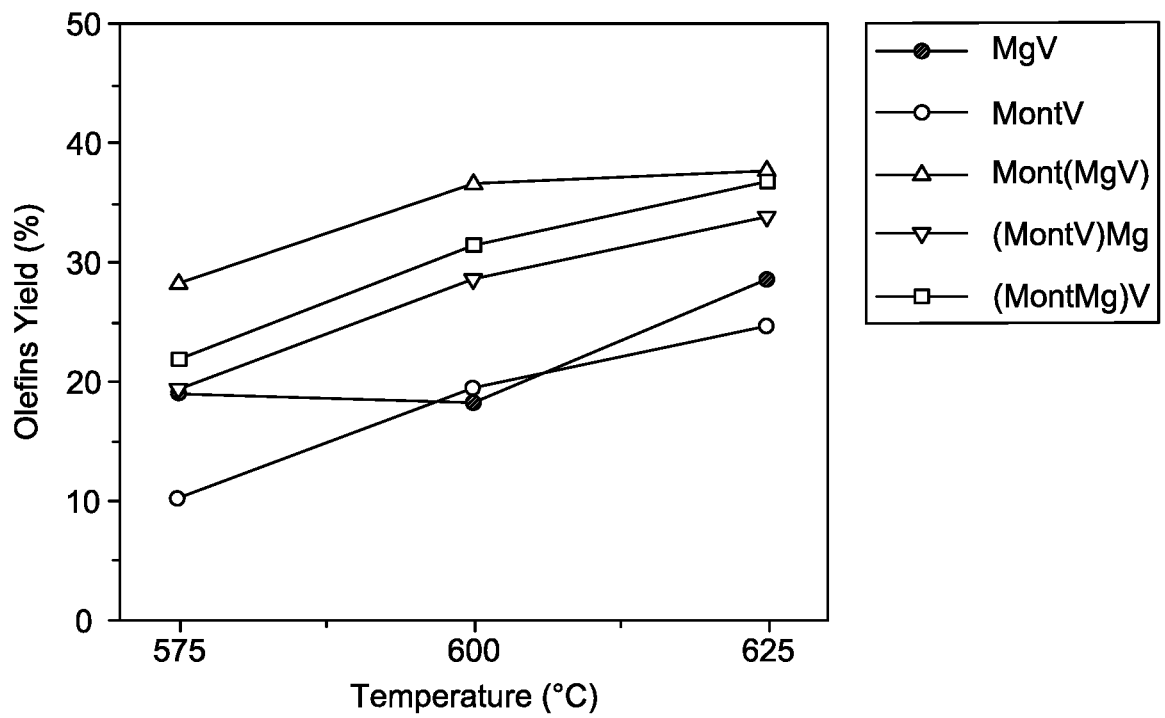
FIG. 12E is a plot of olefin yield depicting variation in the catalytic performance of the various catalysts with temperature, according to certain embodiments.
Figure 12F:
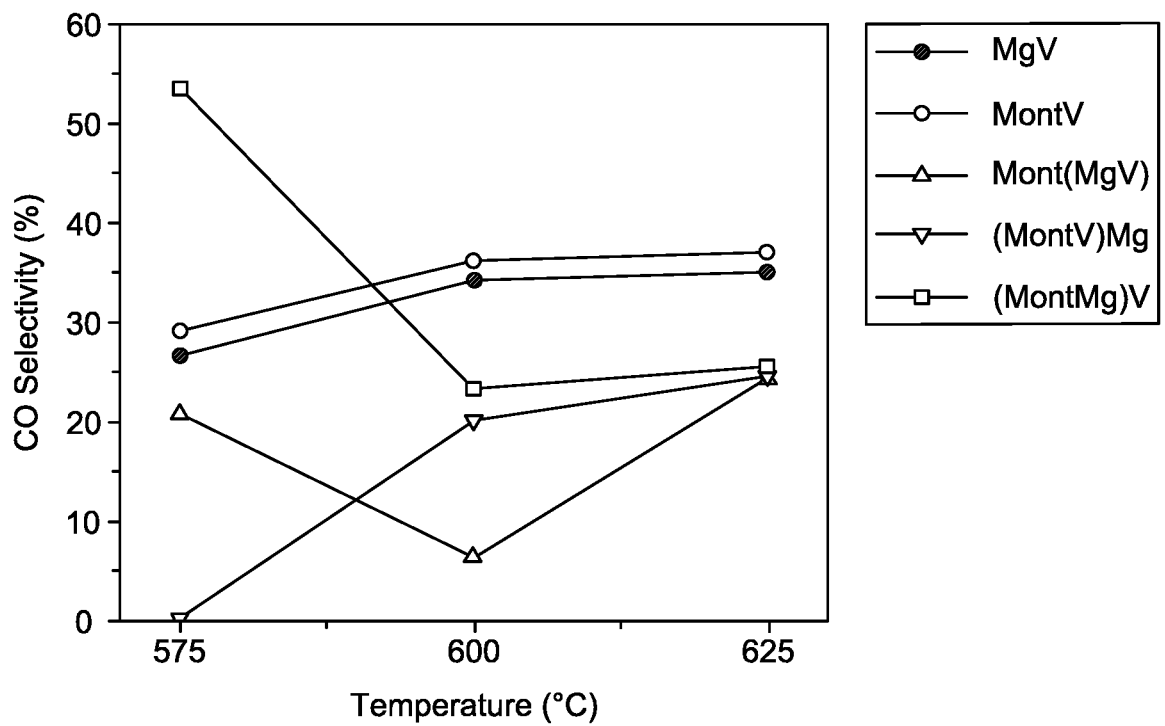
FIG. 12F is a plot of CO selectivity with temperature depicting the variation in the catalytic performance of the various catalysts with temperature, according to certain embodiments.

FIG. 12A depicts the catalytic performance of the integrated catalysts derived via combining the two support materials. It is evident that the propane conversion improved compared to those of MontV and MgV catalysts (FIG. 12A). Typically, Mont(MgV) and (MontMg)V realized around 56.8 and 55.3% conversions at 625° C., respectively. A similar trend was observed for the CO$_2$ conversions and propylene selectivity (FIG. 12B and FIG. 12C, respectively), and the variations become smaller as temperature increases. The propylene yields of all the integrated catalysts were relatively higher, and they varied between (27.4-28.8%), while those of MontV and MgV vary between (18.7-19.6%) (FIG. 12D). Similar trend can be seen observed for the total olefin yields, as depicted on FIG. 12E. According to FIG. 12F, the integrated catalysts showed higher performance in suppressing the selectivity of CO product to values between 24.5-25.7%. This is partly attributed to the modulation in the coordination environment of the VO$_x$ species that led to fewer polymerized species, as evident from UV-vis analysis. Moreover, it may be related that their reduction peaks derived from H$_2$-TPR shifted to lower temperature ranges compared to those of the MgV and the MontV catalysts.

Figure 13A:
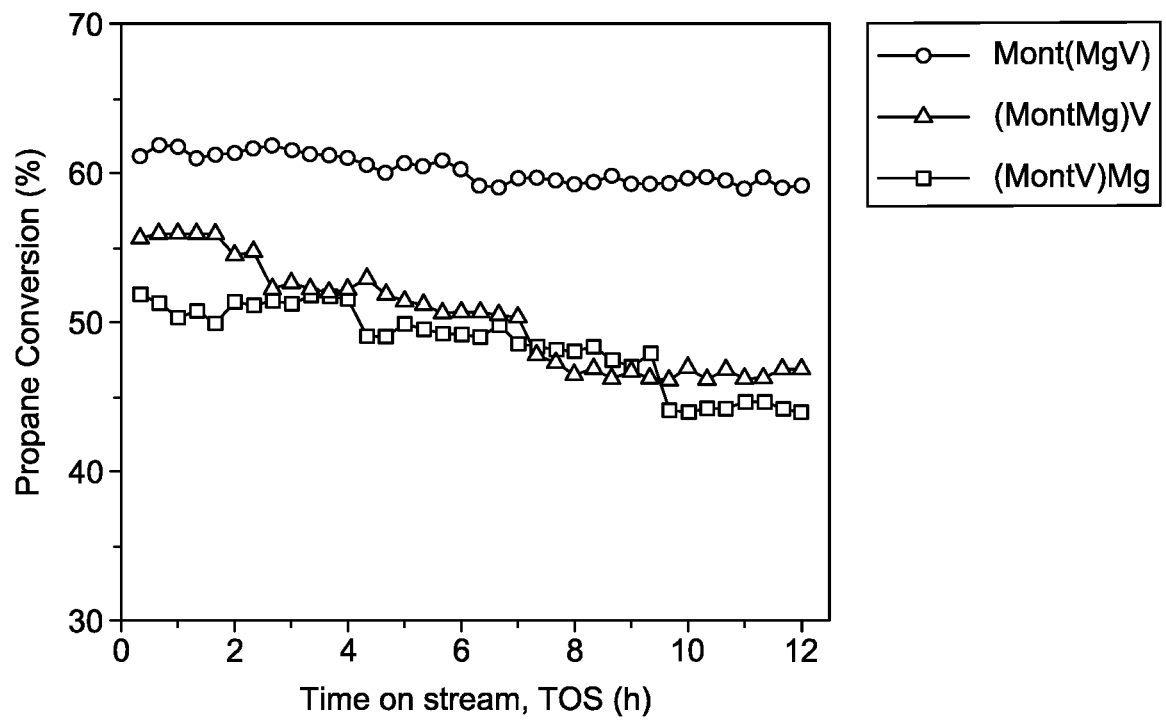
FIG. 13A is a plot depicting catalytic stability of the integrated (MontV)Mg, Mont(MgV), and (MontMg)V catalysts in terms of propane conversion over 12 hours time on stream (TOS), according to certain embodiments.
Figure 13B:
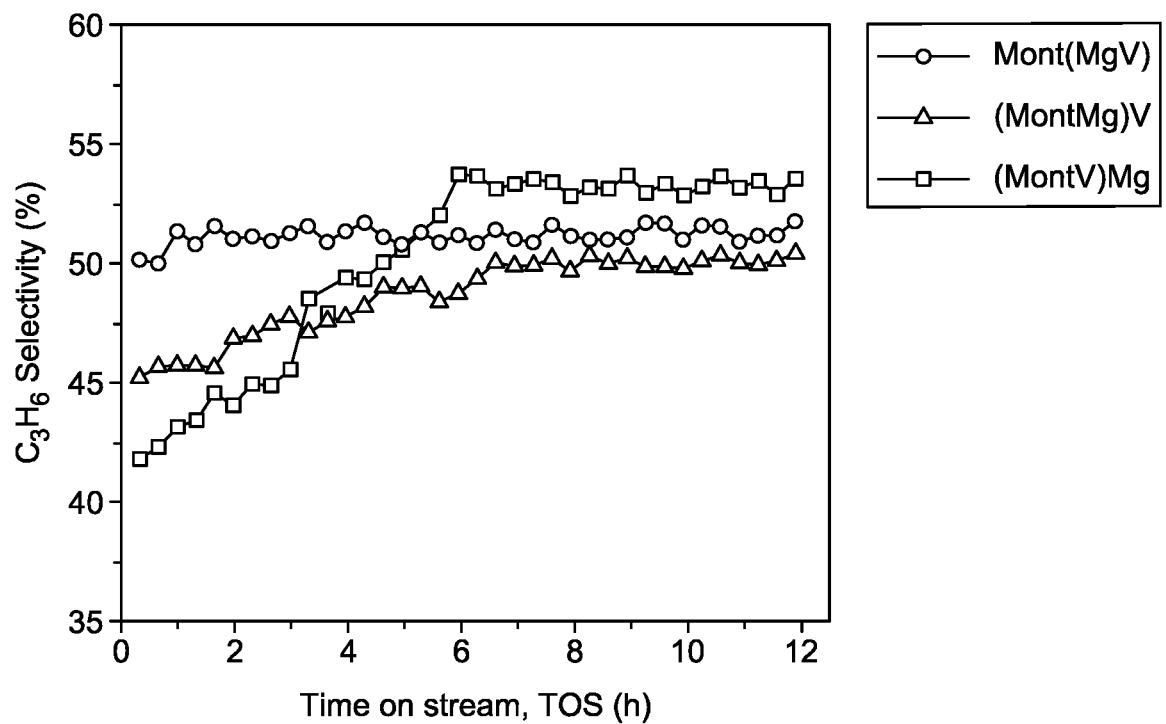
FIG. 13B is a plot depicting catalytic stability of the integrated (MontV)Mg, Mont(MgV), and (MontMg)V catalysts in terms of propylene selectivity over 12 hours TOS, according to certain embodiments.
Figure 13C:
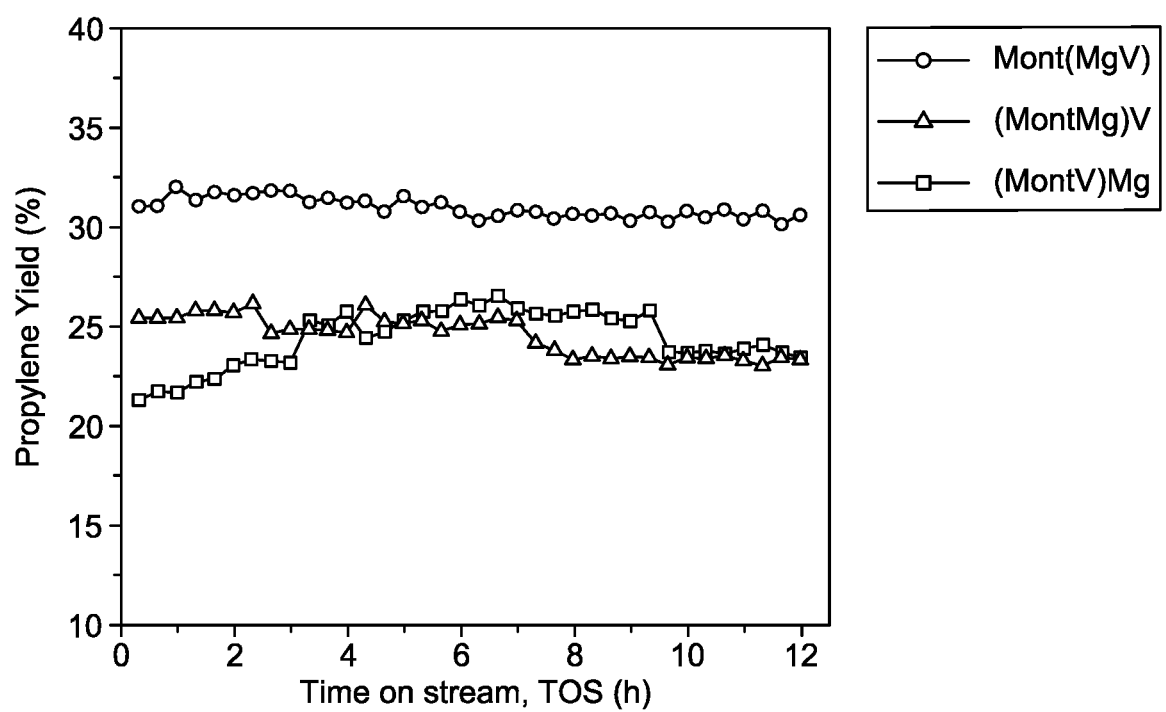
FIG. 13C is a plot depicting catalytic stability of the integrated (MontV)Mg, Mont(MgV), and (MontMg)V catalysts in terms of propylene yield over 12 hours of TOS, according to certain embodiments.

The catalytic stability of the integrated catalysts was investigated over 12 h TOS. From FIG. 13A, (MontV)Mg, and (MontMg)V showed initial propane conversions of 51.9 and 55.7%, respectively, and the performances gradually declined due to possible deactivation to around less than 85% of the initial. Conversely, the Mont(MgV) catalyst exhibited a more stable propane conversion that only depreciated to 97% of the initial. This reveals that integrating the individual montmorillonite and MgO substantially impacts the nature of the catalytic performances of the derived catalysts. FIG. 13B depicts the changes in propylene selectivity with time for the catalysts. It can be observed that the significant decline in activity of the (MontV)Mg and (MontMg)V catalysts was accompanied by continuous improvement in propylene selectivity within the first 7 h. Afterwards, selectivity remained steady at around 53.3 and 49.8%, respectively. This behavior could be attributed to the promotional effect of deposited coke on the stability of CO$_2$-ODH catalysts. The phenomenon involves the gradual encapsulation of the unselective active sites by a few layers of deposited coke coupled with the possible formation of carbonyl/quinone functional groups under oxidizing atmosphere. Depending on the nature of catalysts, highly acidic supports such as alumina could be coked deliberately to improve their olefin selectivity. The Mont(MgV) catalyst displayed a stable propylene selectivity of 51.7% (FIG. 13C). Overall, the catalyst exhibited a remarkable 31% yield to propylene without observable deactivation for 12 h TOS.

Example 20: TGA and Raman Analysis of Spent Catalysts

Figure 14A:
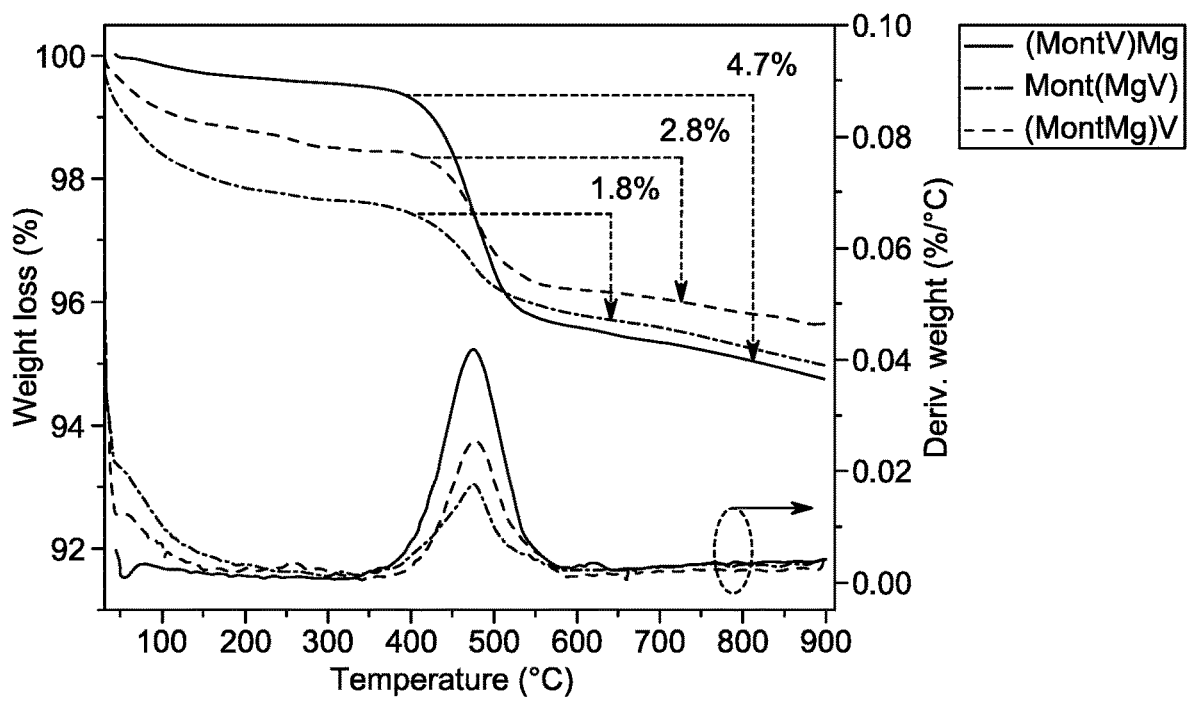
FIG. 14A is a thermal gravimetric analysis (TGA) plot of spent (MontV)Mg, Mont(MgV) and (MontMg)V spent catalysts derived after 12 hours of TOS, according to certain embodiments.
Figure 14B:
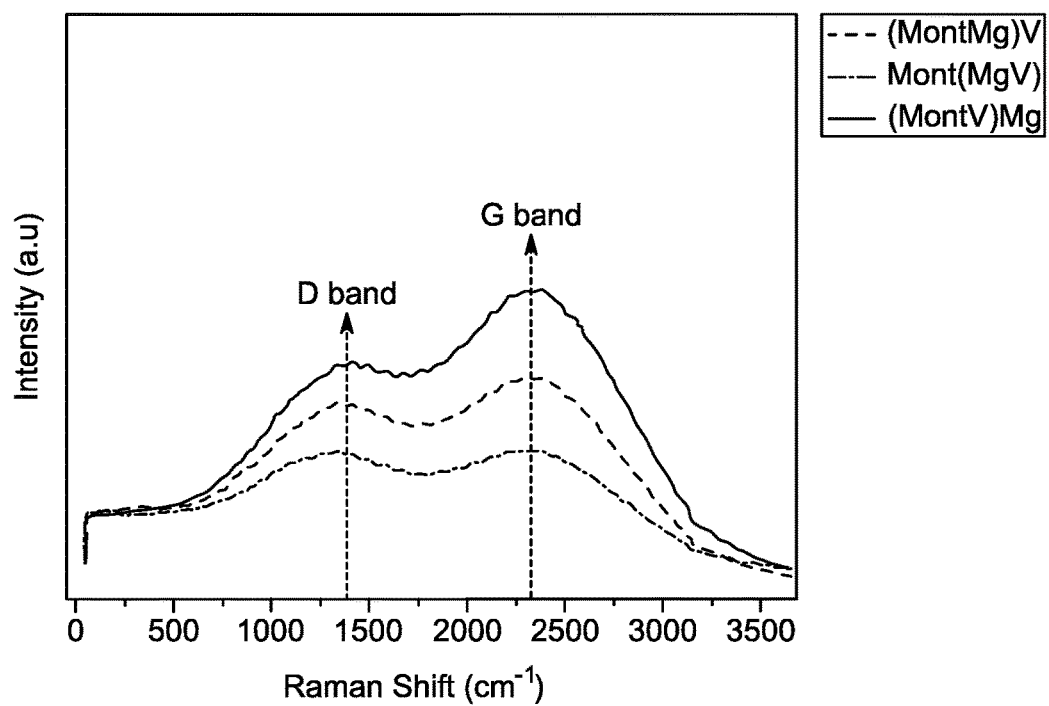
FIG. 14B shows Raman spectra of the (MontV)Mg, Mont(MgV) and (MontMg)V spent catalysts derived after 12 hours with TOS, according to certain embodiments.

The extent of coke formation over the integrated catalysts after 12 h time on stream was probed using TGA analysis and Raman spectroscopy. From FIG. 14A, the TGA reveals all the catalysts experienced only a small amount of weight loss due to possible coke. Remarkably, the Mont(MgV) catalyst exhibited the least, only about 1.8%. This may not be surprising owing to the highly stable catalytic performance it displayed. As depicted in FIG. 14B, the Raman spectra corroborated the observed trend in TGA analysis. Usually, the ratio of the D and G band intensities that appeared at 1396 and 2364 nm indicates the disorder on the surfaces of spent catalysts due to carbon deposition. It can be observed that the extent of coke deposition over the catalysts follows the order Mont(MgV)<(MontMg)< (MontV)Mg. The highest coke formation of the (MontV)Mg may be related to highly mobile oxygen species on its surface, as evident from H$_2$-TPR analysis.

CO$_2$-mediated oxidative dehydrogenation (CO$_2$-ODH) of propane was investigated over a series of vanadium-based catalysts supported on montmorillonite (Mont) and MgO. The catalysts were derived via a facile and template-free strategy involving physical grinding of the constituents and two-phase calcination protocols. As for single support catalysts, MgV and MontV were found to be relatively more active and more selective, respectively. Among all the catalysts, Mont(MgV) engineered via rationally integrating MgV with Mont resulted in the best CO$_2$-ODH catalytic performance. During 12 h time on stream performance, the catalyst exhibited stable propane conversion and propylene selectivity of around 59% and 52%, respectively. The nature of the individual supports and the manner of integrating them significantly modulated the nature of the evolved VO$_x$ species regulated the amount of both acid and basic sites and the surface reducibility of the catalysts.

Numerous modifications and variations of the present disclosure are possible in light of the above teachings. It is therefore to be understood that within the scope of the appended claims, the invention may be practiced otherwise than as specifically described herein.

The invention claimed is:

1. A method of making an active catalyst composition containing a first vanadium catalyst and a second vanadium catalyst, comprising:
   mixing at least one support with a vanadium oxide precursor and grinding thereby at least partially embedding the vanadium oxide precursor particles in different layers and surfaces of the at least one support to form a first precursor;
   wherein a weight ratio of the at least one support to the vanadium oxide precursor is in a range of 100:1 to 10:1;
   mixing the first precursor and a first solvent to form a first mixture;
   grinding the first mixture and drying at a temperature of 60 to 105° C.; and calcining the first mixture after the drying at a temperature of at least 300° C. thereby allowing the vanadium oxide precursor particles embedded in different layers and surfaces of the at least one support to decompose in situ to generate vanadium oxide ($VO_x$) particles embedded in the at least one support and form the first vanadium catalyst;

wherein the vanadium oxide particles have an average particle size of 50 to 200 nanometers (nm), and are uniformly distributed throughout the first vanadium catalyst;

wherein 0<x<3;

wherein the at least one support comprises a smectite clay and a metal oxide; and mixing the first vanadium catalyst with the second vanadium catalyst to form the active catalyst composition.

2. The method of claim 1, wherein the vanadium oxide precursor is at least one selected from the group consisting of vanadium acetylacetonate, ammonium vanadate, vanadyl oxalate, vanadium pentoxide, vanadium monoethanolamine, vanadium chloride, vanadium trichloride oxide, vanadyl sulfate, vanadium antimonate, antimony vanadate, vanadium oxyacetylacetonate, vanadium oxyacetate, vanadium oxyhalide, and vanadium oxytriisopropoxide.

3. The method of claim 1, wherein the vanadium oxide ($VO_x$) particles comprise vanadium monoxide (VO), vanadium trioxide ($V_2O_3$), vanadium dioxide ($VO_2$), and vanadium pentoxide ($V_2O_5$).

4. The method of claim 1, wherein the first solvent is at least one selected from the group consisting of a ketone solvent, an ester solvent, an alcohol solvent, an amide solvent, and an ether solvent.

5. The method of claim 1, wherein the first precursor is present in the first mixture at a concentration of 1 to 40 wt. % based on a total weight of the first mixture.

6. The method of claim 1, wherein the smectite clay comprises at least one clay selected from the group consisting of montmorillonite (Mont), nontronite, beidellite, bentonite, bolcon score, laponite, hectorite, saponite, soconite, magadiite, kenyaite, stevensite, vermiculite, halloysite, and hydrotalcite.

7. The method of claim 1, wherein the smectite clay is montmorillonite, wherein the montmorillonite has a delaminated-pillared structure, and wherein the delaminated-pillared structure comprising:

an aluminosilicate framework having a tetrahedral silicate layer and an octahedral aluminium hydroxide layer; and a plurality of exchangeable intercalated cations between two adjacent aluminosilicate frameworks.

8. The method of claim 1, wherein the metal oxide comprises at least one selected from the group consisting of magnesium oxide (MgO), aluminum oxide ($Al_2O_3$), and titanium oxide ($TiO_2$).

9. The method of claim 1, further comprising:

forming the second vanadium catalyst by:
mixing the first vanadium catalyst with a second support and grinding to form a second precursor;
wherein a weight ratio of the first vanadium catalyst to the second support is in a range of 2:1 to 1:2;
wherein the first vanadium catalyst is complexed with the second support;
mixing the second precursor and a second solvent to form a second mixture;
grinding the second mixture and drying at a temperature of 60 to 105° C.; and calcining the second mixture after the drying at a temperature of at least 300° C. to form the second vanadium catalyst;
wherein the second support comprises a smectite clay and a metal oxide.

10. The method of claim 1, wherein the smectite clay is montmorillonite (Mont), wherein the metal oxide is MgO, and wherein the active catalyst composition is at least one selected from the group consisting of a MgO supported vanadium (MgV), a Mont supported vanadium (MontV), a Mont supported vanadium supported on MgO((MontV)Mg), a MgO supported vanadium supported on Mont (Mont (MgV)), and a Mont/MgO co-supported vanadium ((MontMg)V).

11. The method of claim 1, wherein the active catalyst composition has a multi-layered mesoporous structure.

12. The method of claim 1, wherein the active catalyst composition has a specific surface area in a range of 50 to 200 square meters per gram ($m^2/g$).

13. The method of claim 1, wherein the active catalyst composition has a cumulative specific pore volume in a range of 0.1 to 0.8 cubic centimeters per gram ($cm^3/g$).

14. The method of claim 1, wherein the active catalyst composition has an average pore diameter of 50 to 300 angstroms (Å).

15. A method for producing propylene via oxidative dehydrogenation (ODH) of propane, comprising:

introducing a feed gas stream containing $CO_2$ and propane into a reactor containing the active catalyst composition prepared by the method of claim 1;

passing the feed gas stream through the reactor in the presence of the active catalyst composition at a temperature of 300 to 900° C. to convert at least a portion of the propane to propylene and produce a propylene-containing gas stream leaving the reactor; and separating the propylene from the propylene-containing gas stream.

16. The method of claim 15, wherein a volume ratio of $CO_2$ to propane in the feed gas stream is in a range of 1:10 to 10:1.

17. The method of claim 15, wherein the propylene-containing gas stream further comprises methane, ethane, ethylene, propane, carbon monoxide, carbon dioxide, hydrocarbon containing $C_4$-$C_5$, and aromatics.

18. The method of claim 15, having a propane conversion to propylene of up to 80 wt. % based on an initial weight of the propane in the feed gas stream.

19. The method of claim 15, having a propylene yield of up to 40% based on the propane conversion according to equation $Y_3=(X_{C_3H_8}*S_3)\times100\%$;

wherein $X_{C_3H_8}$ denotes the propane conversion to propylene; and wherein $S_3$ denotes the propylene selectivity.

20. The method of claim 15, having a propylene selectivity of up to 70% based on the propane conversion according to equation $$S_3 = \frac{n_3}{n_{C_3H_{8_{in}}} - n_{C_3H_{8_{out}}}} \times 100\%;$$

wherein $S_3$ denotes the propylene selectivity;

wherein $(n_{C_3H_8})_{in}$ and $(n_{C_3H_8})_{out}$ denote the inlet and outlet moles of the propane in the feed gas stream containing $CO_2$ and propane, respectively; and wherein $n_3$ denote moles of the propylene in the propylene-containing gas stream leaving the reactor.

* * * * *